US009189678B2

(12) United States Patent
Tsunomori et al.

(10) Patent No.: US 9,189,678 B2
(45) Date of Patent: Nov. 17, 2015

(54) MEDICAL IMAGE PROCESSOR AND STORAGE MEDIUM

(71) Applicants: Konica Minolta, Inc., Tokyo (JP); Tohoku University, Sendai-shi, Miyagi (JP)

(72) Inventors: Akinori Tsunomori, Kodaira (JP); Hisatake Okada, Tachikawa (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/387,415

(22) PCT Filed: Mar. 27, 2013

(86) PCT No.: PCT/JP2013/058919
§ 371 (c)(1),
(2) Date: Sep. 23, 2014

(87) PCT Pub. No.: WO2013/146843
PCT Pub. Date: Oct. 3, 2013

(65) Prior Publication Data
US 2015/0086103 A1    Mar. 26, 2015

(30) Foreign Application Priority Data

Mar. 30, 2012  (JP) ................. 2012-078722

(51) Int. Cl.
G06K 9/00 (2006.01)
G06T 7/00 (2006.01)
G01N 21/64 (2006.01)

(52) U.S. Cl.
CPC ............ *G06K 9/0014* (2013.01); *G06T 7/0012* (2013.01); *G01N 21/6458* (2013.01);
(Continued)

(58) Field of Classification Search
None
See application file for complete search history.

(56) References Cited

U.S. PATENT DOCUMENTS 8,428,331 B2 *  4/2013  DiMarzio .......... G02B 21/0004
                                              382/133
2002/0081014 A1 *  6/2002  Ravkin ............... G01N 15/1475
                                              382/134

(Continued)

FOREIGN PATENT DOCUMENTS

JP    2008-268027 A    11/2008
JP    2009-115599 A     5/2009

(Continued)

OTHER PUBLICATIONS

Brügmann, Anja, et al. "Digital image analysis of membrane connectivity is a robust measure of HER2 immunostains." Breast cancer research and treatment 132.1 (2012): 41-49.*

(Continued)

*Primary Examiner* — Bhavesh Mehta
*Assistant Examiner* — Sean Conner
(74) *Attorney, Agent, or Firm* — Lucas & Mercanti, LLP

(57) ABSTRACT

A medical image processor and a storage medium are shown. According to one implementation, the medical image processor includes the following. An input unit is used to input a cell shape image and a fluorescent image showing expression of a specific protein. A cell nucleus extracting unit extracts a cell nucleus. A fluorescent bright point extracting unit extracts a fluorescent bright point. A region estimating unit sets a predetermined region. When the set region does not overlap with another, it is estimated to include one cell. When a plurality of the set regions overlap, it is estimated to include a plurality of cells. A feature amount calculating unit calculates a feature amount. A determining unit determines whether each estimated cell region is cancer and determines an expression status in the region based on the calculated feature amount. An output unit outputs a determination result.

5 Claims, 22 Drawing Sheets

(52) U.S. Cl.
CPC ............... *G06T 2207/10061* (2013.01); *G06T 2207/10064* (2013.01); *G06T 2207/20221* (2013.01); *G06T 2207/30024* (2013.01); *G06T 2207/30096* (2013.01)

(56) References Cited

U.S. PATENT DOCUMENTS

| | | | | |
|---|---|---|---|---|
| 2003/0231791 | A1* | 12/2003 | Torre-Bueno | G01N 21/6428 382/133 |
| 2005/0163359 | A1* | 7/2005 | Murao | G01N 15/1475 382/128 |
| 2005/0265588 | A1* | 12/2005 | Gholap | G06K 9/00127 382/128 |
| 2007/0219769 | A1* | 9/2007 | Herzog | G06K 9/0014 703/11 |
| 2008/0032325 | A1* | 2/2008 | DiMarzio | G02B 21/18 435/29 |
| 2008/0212866 | A1* | 9/2008 | Lett | G01N 21/6428 382/133 |
| 2008/0240539 | A1* | 10/2008 | George | G01N 21/47 382/133 |
| 2009/0196482 | A1* | 8/2009 | Kobayashi | G01N 21/6458 382/133 |
| 2010/0290692 | A1* | 11/2010 | Macaulay | G06T 7/0012 382/133 |
| 2011/0211741 | A1* | 9/2011 | Nakano | G01N 15/1434 382/128 |
| 2011/0249883 | A1* | 10/2011 | Can | G06K 9/0014 382/133 |
| 2012/0112098 | A1* | 5/2012 | Hoyt | B82Y 30/00 250/459.1 |

FOREIGN PATENT DOCUMENTS

| | | |
|---|---|---|
| JP | 2009-115813 A | 5/2009 |
| WO | WO2004/042392 A1 | 5/2004 |

OTHER PUBLICATIONS

English translation of the International Preliminary report on patentability (Written Opinion) dated Jul. 2, 2013.

* cited by examiner

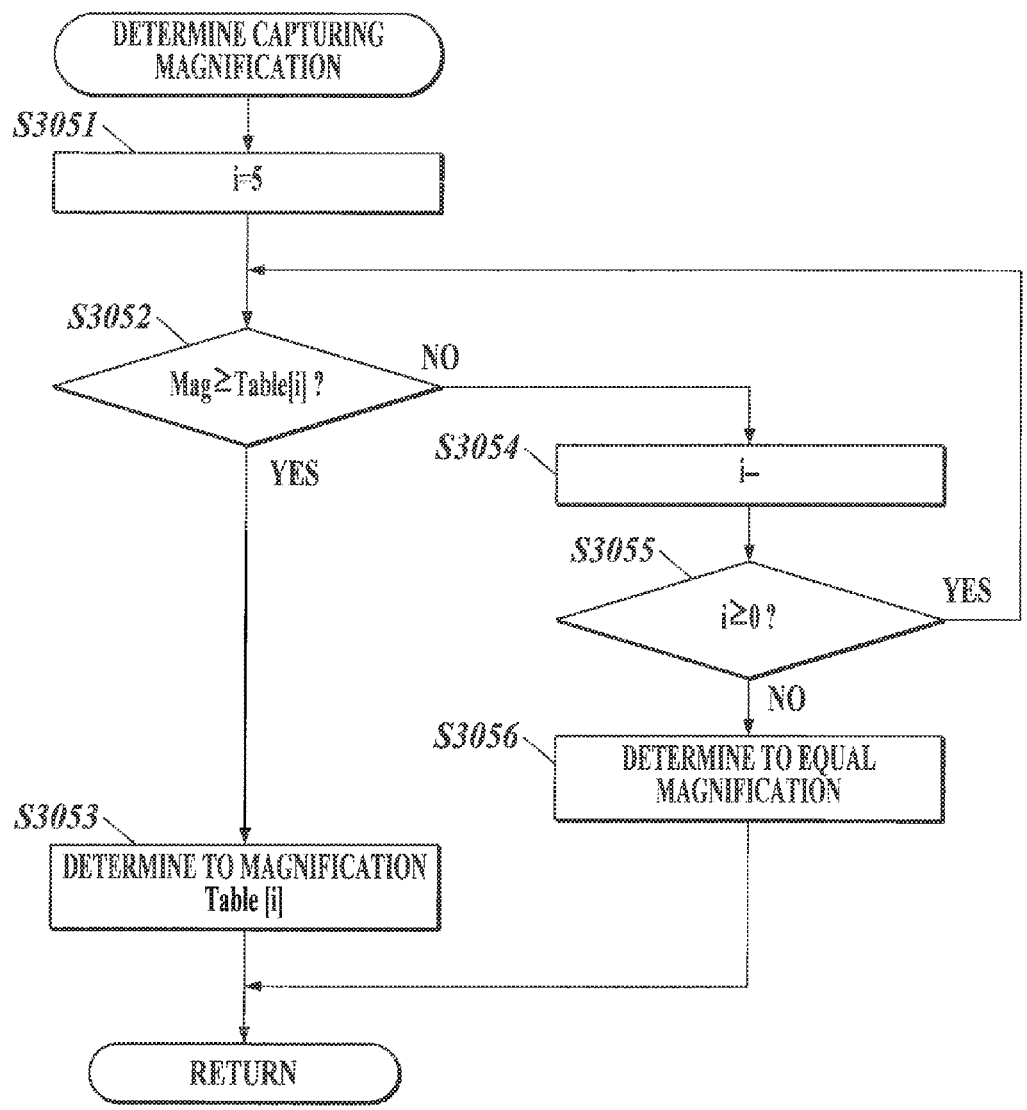

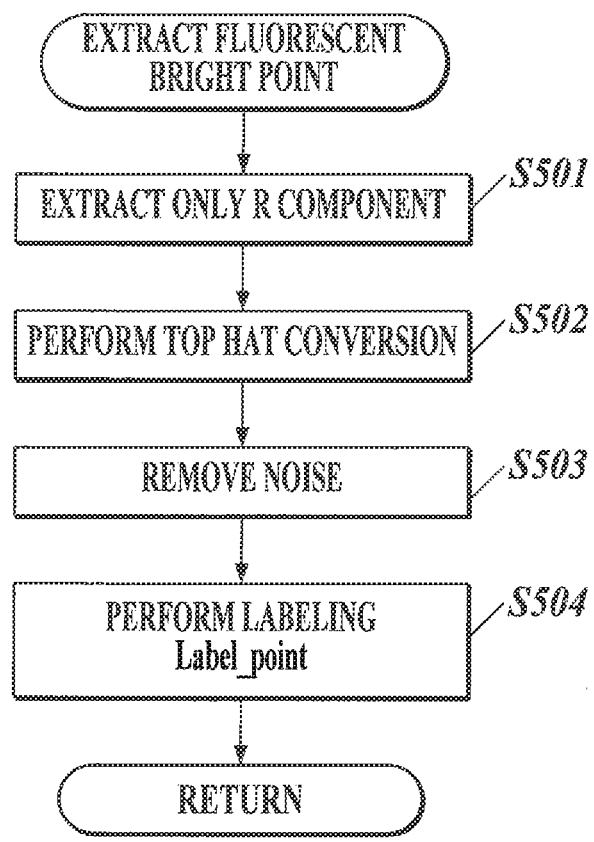

MEDICAL IMAGE PROCESSOR AND STORAGE MEDIUM

CROSS REFERENCE TO RELATED APPLICATION

This Application is a 371 of PCT/JP2013/058919 filed on Mar. 27, 2013 which, in turn, claimed the priority of Japanese Patent Application No. JP2012-078722 filed on Mar. 30, 2012 both applications are incorporated herein by reference.

TECHNICAL FIELD

The present invention relates to a medical image processor and a program.

BACKGROUND ART

In pathological diagnosis, first, after processing of dehydrating the obtained tissue so as to be fixed and blocking with paraffin, the above is cut into thin pieces with a thickness of 2 to 8 µm, the paraffin is removed, and the above is stained to observe with a microscope. The pathologist performs diagnosis based on morphologic information such as change in size and shape of a nucleus of a cell, change in pattern as a tissue, etc., and stain information in the microscopic image. Methods known as the tissue staining method used in pathological diagnosis include a conventional chromatic staining method (for example, Hematoxylin and Eosin staining; hereinafter referred to as HE staining) and a chromatic staining method using enzyme (for example, DAB (diaminobenzidine) staining).

In pathological diagnosis, specifying the protein overexpressing in the tissue slice and its expression amount may be very important information for prognostic expectation and determining the future treatment plan.

For example, HER2 protein coding HER2 gene is a receptor type glycoprotein which penetrates the cell membrane, is composed of 3 domains which are extracellular, transmembrane, and intracellular, is activated by phosphorylating of tyrosine residue when bonded with a growth factor, and is said to be involved in proliferation and malignant alteration of cells through signaling pathways. Overexpression of HER2 protein can be seen in breast cancer, lung cancer, colon cancer, stomach cancer, bladder cancer, etc.

HER2 protein is considered to be a prognostic factor of breast cancer, and it is known that especially in a case where lymph node metastasis is positive, the prognosis of cases where HER2 is positive is significantly poor. HER2 protein is also gathering attention as an information factor for deciding adaptation of a molecularly targeted drug (trastuzumab) and as a result prediction factor of anticancer drugs such as anthracycline type, taxane type, etc.

Typically, overexpression of HER2 protein is examined by an immunohistochemical method (IHC method) and overexpression of HER2 gene is examined by FISH method. According to the HER examination guideline, first, positive, negative, boundary region is discriminated by a simple IHC method, and when the result is positive, it is decided that trastuzumab is provided. When the result is in the boundary region with the IHC method, further examination is done to discriminate positive and negative by the FISH method.

Comparing the IHC method and the FISH method, the IHC method is easier, but there is the problem that accuracy is low. Turning to the FISH method, the accuracy is high, but the process is troublesome, and the cost is high. In other words, there are needs for development of a method of an IHC method which has the same accuracy as the FISH method. Moreover, there are needs for development of a method where the dependence on the person is low and which can be automated.

For example, Patent Document 1 describes a system where a cell nucleus is extracted from an image of biological tissue stained by the DAB method, a cell membrane is specified from an image of biological tissue based on the cell nucleus, a stained state of a cell membrane is determined, and expression of HER2 protein is evaluated based on the result of determination.

PRIOR ART DOCUMENT

Patent Document

Patent Document 1: Japanese Patent Application Laid-Open Publication No. 2009-115599

DISCLOSURE OF THE INVENTION

Problems to be Solved by the Invention

However, in the DAB method, there is increase due to the enzyme and the method lacks quantitative capabilities. Therefore, according to the technique described in patent document 1, it is not possible to accurately understand expression amount of the HER2 protein. Moreover, according to patent document 1, the expression of protein is evaluated in a region specified by the user as a tumor region from the entire image. Therefore, it is not possible to prevent oversight of the tumor region by the user.

The problem to be solved by the present invention is to enable a physician to efficiently understand a cancer region where there is overexpression of a specific protein from the entire image of a tissue slice.

Means for Solving the Problem

In order to solve the above problems, according to a first aspect of the present invention, there is provided a medical image processor including:

an input unit to input a cell shape image showing a shape of a cell in a tissue slice and a fluorescent image showing expression of a specific protein in a same range of the tissue slice as a fluorescent bright point;

a cell nucleus extracting unit which extracts a region of a cell nucleus from the cell shape image;

a fluorescent bright point extracting unit which extracts a fluorescent bright point from the fluorescent image;

a region estimating unit which sets a predetermined region which includes from a centroid of a region of each cell nucleus extracted by the cell nucleus extracting unit to an expression region of the specific protein in a cell membrane periphery, wherein when the set region does not overlap with another set region, the set region is estimated to be a cell region including one cell, and when a plurality of the set regions overlap with each other, a region surrounded by an outer circumference of the plurality of overlapping regions is estimated to be a cell region including a plurality of cells;

a feature amount calculating unit which calculates a feature amount regarding each cell region based on a cell nucleus and a fluorescent bright point included in each cell region estimated by the region estimating unit;

a determining unit which determines whether each cell region estimated by the region estimating unit is cancer and which determines an expression status of the specific protein in the region determined to be cancer, the above determined based on the calculated feature amount; and an output unit which outputs a determination result by the determining unit.

Preferably, in the medical image processor, the region set by the region estimating unit is a circular region with a centroid of the region of each cell nucleus extracted by the cell nucleus extracting unit as a center and a predetermined radius including the expression region of the specific protein in the cell membrane periphery.

Preferably, in the medical image processor, the feature amount calculating unit calculates an area which each cell nucleus occupies in each cell region and/or an index value which shows uneven distribution of the cell nucleus in each cell region based on the cell nucleus included in each cell region estimated by the region estimating unit and calculates a density of the fluorescent bright point in each cell region based on the fluorescent bright point included in each cell region; and the determining unit determines whether each cell region is cancer based on the area which each cell nucleus occupies in each cell region and/or the index value which shows uneven distribution of the cell nucleus in each cell region, and determines the expression status of the specific protein in the cell region determined to be cancer based on the density of the fluorescent bright point in the cell region.

Preferably, in the medical image processor, the determining unit classifies the expression status of the specific protein in the cell region determined to be cancer into a plurality of levels based on whether the calculated feature amount of the fluorescent bright point in the cell region determined to be cancer exceeds a plurality of predetermined thresholds; and the output unit outputs an image dividing the cell region determined to be cancer on the cell shape image in a form according to a classification result of the expression status of the specific protein as the determination result.

According to a second aspect of the present invention there is provided a program for controlling a computer to function as:

an input unit to input a cell shape image showing a shape of a cell in a tissue slice and a fluorescent image showing expression of a specific protein in a same range of the tissue slice as a fluorescent bright point;

a cell nucleus extracting unit which extracts a region of a cell nucleus from the cell shape image;

a fluorescent bright point extracting unit which extracts a fluorescent bright point from the fluorescent image;

a region estimating unit which sets a predetermined region which includes from a centroid of a region of each cell nucleus extracted by the cell nucleus extracting unit to an expression region of the specific protein in a cell membrane periphery, wherein when the set region does not overlap with another set region, the set region is estimated to be a cell region including one cell, and when a plurality of the set regions overlap with each other, a region surrounded by an outer circumference of the plurality of overlapping regions is estimated to be a cell region including a plurality of cells;

a feature amount calculating unit which calculates a feature amount regarding each cell region based on a cell nucleus and a fluorescent bright point included in each cell region estimated by the region estimating unit;

a determining unit which determines whether each cell region estimated by the region estimating unit is cancer and which determines an expression status of the specific protein in the region determined to be cancer, the above determined based on the calculated feature amount; and an output unit which outputs a determination result by the determining unit.

Advantageous Effect of the Invention

According to the present invention, it is possible to efficiently understand a cancer region where there is overexpression of a specific protein from the entire image of a tissue slice.

BRIEF DESCRIPTION OF THE DRAWINGS

FIG. 19 is a flowchart showing a detailed flow of processing in step S305 of FIG. 14;

FIG. 21 is a flow chart showing details of processing of step S5 of FIG. 10;

EMBODIMENT FOR CARRYING OUT THE INVENTION

Embodiments of the present invention are described below with reference to the drawings, however, the present invention is not limited to the illustrated examples.

<Configuration of Pathological Diagnosis Assistance System 100>

Figure 1:
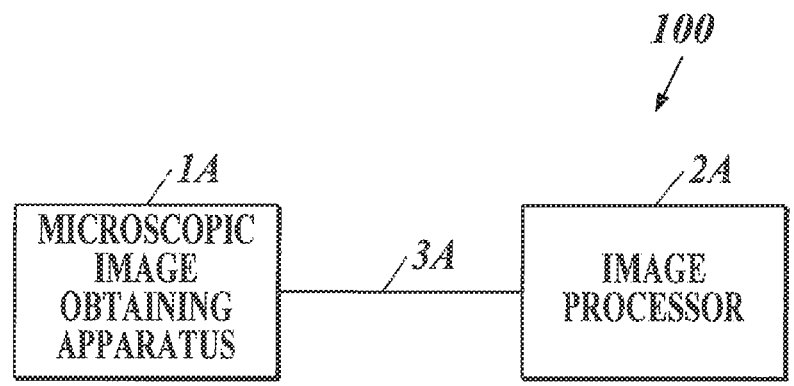
FIG. 1 is a diagram showing a system configuration of a pathological diagnosis assistance system.

FIG. 1 shows an example of an entire configuration of a pathological diagnosis assistance system 100 of the first embodiment. The pathological diagnostic assistance system 100 obtains a microscopic image of a tissue slice of a human body stained with a predetermined staining reagent, and outputs a feature amount quantitatively expressing a specific biological substance in the tissue slice of the observation target by analyzing the obtained microscopic image.

As shown in FIG. 1, the pathological diagnosis assistance system 100 includes a microscopic image obtaining apparatus 1A and an image processor 2A connected to each other through an interface such as a cable 3A so as to be able to transmit and receive data. The method of connecting the microscopic image obtaining apparatus 1A and the image processor 2A is not limited. For example, the microscopic image obtaining apparatus 1A and the image processor 2A can be connected by a LAN (Local Area Network) or can be connected wirelessly.

The microscopic image obtaining apparatus 1A is a well-known optical microscope with a camera. The microscopic image obtaining apparatus 1A obtains the microscopic image of the tissue piece on the slide placed on a slide fixing stage, and transmits the image to the image processor 2A.

The microscopic image obtaining apparatus 1A includes an irradiating unit, an image forming unit, an imaging unit, a communication I/F, etc. The irradiating unit includes a light source, filter, etc., which irradiates light on the tissue slice on the slide placed on the slide fixing stage. The image forming unit includes an ocular lens, an object lens, etc., and forms an image of transmitted light, reflected light, or fluorescence light from the tissue slice on the slide due to the irradiated light. The imaging unit is a camera provided in a microscope which includes a CCD (Charge Coupled Device) sensor, etc., and images an image formed on an image forming face by the image forming unit to generate digital image data (R, G, B image data) of the microscopic image. The communication I/F transmits the generated image data of the microscopic image to the image processor 2A. According to the present embodiment, the microscopic image obtaining apparatus 1A includes a bright field unit combining the irradiating unit and the image forming unit suitable for bright field observation and a fluorescent unit combining the irradiating unit and the image forming unit suitable for fluorescent observation. The bright field/fluorescence can be switched by switching the units.

The microscopic image obtaining apparatus 1A is not limited to a microscope with a camera. For example, a virtual microscope slide creating apparatus which scans a slide on a slide fixing stage of a microscope and obtains a microscopic image of the entire tissue slice can be used (for example, see Japanese Patent Application Laid-Open Publication No. 2002-514319). According to the virtual microscope slide creating apparatus, image data with which the entire image of the tissue slice on the slide can be viewed at once on the display section can be obtained.

The image processor 2A is a medical image processor which analyzes the microscopic image transmitted from the microscopic image obtaining apparatus 1A, calculates the feature amount which quantitatively shows the expression amount of a certain biological substance in the tissue slice of the observation target, and outputs the calculated feature amount.

Figure 2:
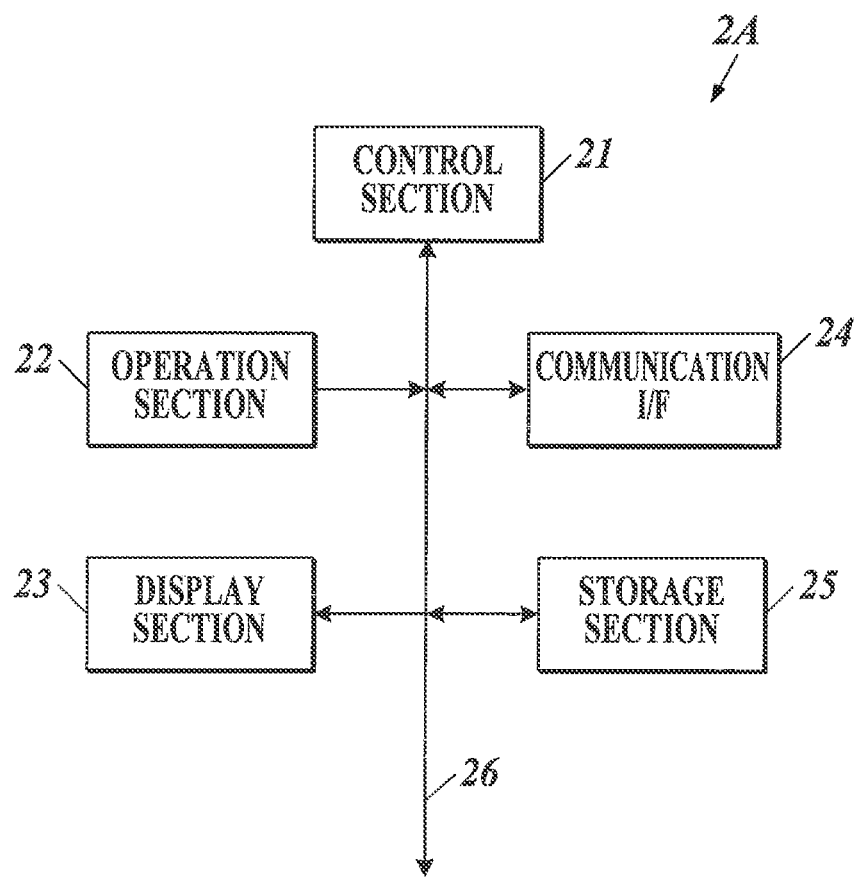
FIG. 2 is a block diagram showing a functional configuration of an image processor of FIG. 1.

FIG. 2 shows an example of a functional configuration of the image processor 2A. As shown in FIG. 2, the image processor 2A includes a control section 21, an operation section 22, a display section 23, a communication I/F 24, a storage section 25, and the like, and each section is connected through a bus 26.

The control section 21 includes a CPU (Central Processing Unit), a RAM (Random Access Memory), and the like, performs various processing in coordination with various programs stored in the storage section 25, and collectively controls the operation of the image processor 2A. For example, the control section 21 performs image analysis processing (see FIG. 10) in coordination with a program stored in the storage section 25, and realizes functions as a cell nucleus extracting unit, fluorescent bright point extracting unit, region estimating unit, feature amount calculating unit, and determining unit.

The operating section 22 includes a keyboard provided with character input keys, numeric input keys and various function keys and a pointing device such as a mouse, and outputs pressed signals of the keys pressed on the keyboard and operation signals of the mouse, and outputs the signals as the input signal to the control section 21.

The display section 23 includes a monitor such as a CRT (Cathode Ray Tube), LCD (Liquid Crystal Display), etc., and displays various screens according to an instruction of a display signal input from the control section 21. According to the present embodiment, the display section 23 functions as an output unit to output the calculated feature amount.

The communication I/F 24 is an interface for transmitting and receiving data with external devices such as the microscopic image obtaining apparatus 1A. The communication I/F 24 functions as the input unit of the bright field image and the fluorescent image. According to the present embodiment, the communication I/F 24 functions as an input unit.

The storage section 25 includes, for example, an HDD (Hard Disk Drive), a nonvolatile semiconductor memory, etc. The storage section 25 stores various programs and various pieces of data as described above. For example, the storage section 25 stores various pieces of data such as a magnification table 251 used in the later described image analysis processing.

Other than the above, the image processor 2A can include a LAN adaptor, a router, etc., and can be connected to external devices through a communication network such as a LAN.

The image processor 2A of the present embodiment analyses the bright field image (HE stain image) and the fluorescent image transmitted from the microscopic image obtaining apparatus 1A.

Figure 3:
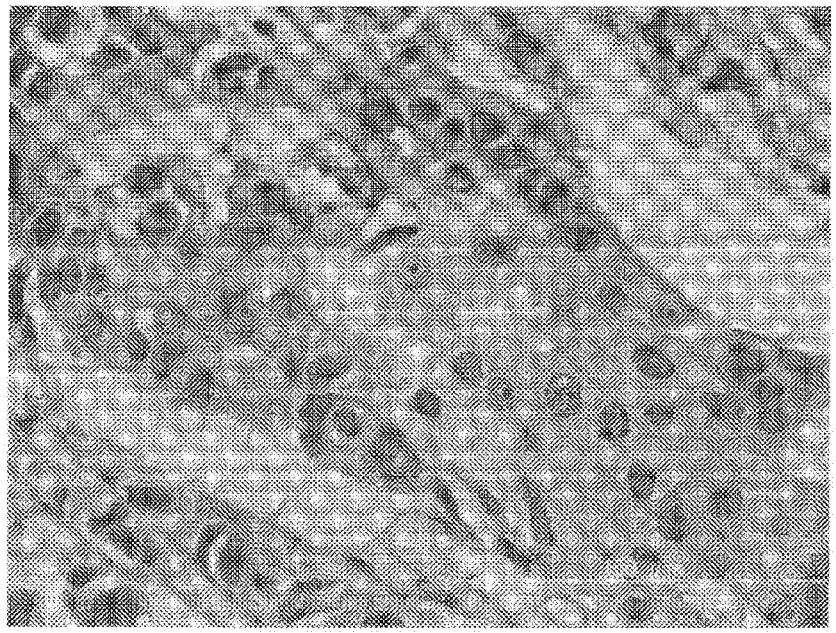
FIG. 3 is a diagram showing an example of a bright field image.

The bright field image is a microscopic image obtained by forming an enlarged image of a tissue slice with HE (hematoxylin-eosin) stain in a bright field in the microscopic image obtaining apparatus 1A and capturing the image. Hematoxylin is a blue purple dye and stains the cell nucleus, bone tissue, a portion of cartilage tissue, serous fluid component etc. (basophilic tissue, etc.). Eosin is a red to pink dye and stains cytoplasm, connective tissue of soft tissue, red blood cell, fibrin, endocrine granule, etc. (eosinophilic tissue, etc.). FIG. 3 shows an example of a bright field image capturing the tissue slice with HE stain. As shown in FIG. 3, in the bright field image capturing the tissue slice with the HE stain, the shape of the cell in the tissue slice appears. The cell nucleus is shown with a darker color than the surrounding cytoplasm (blue purple color) to be distinguished from the surrounding portion, and in the bright field image, it is possible to clearly see the shape of the cell nucleus.

Figure 4:
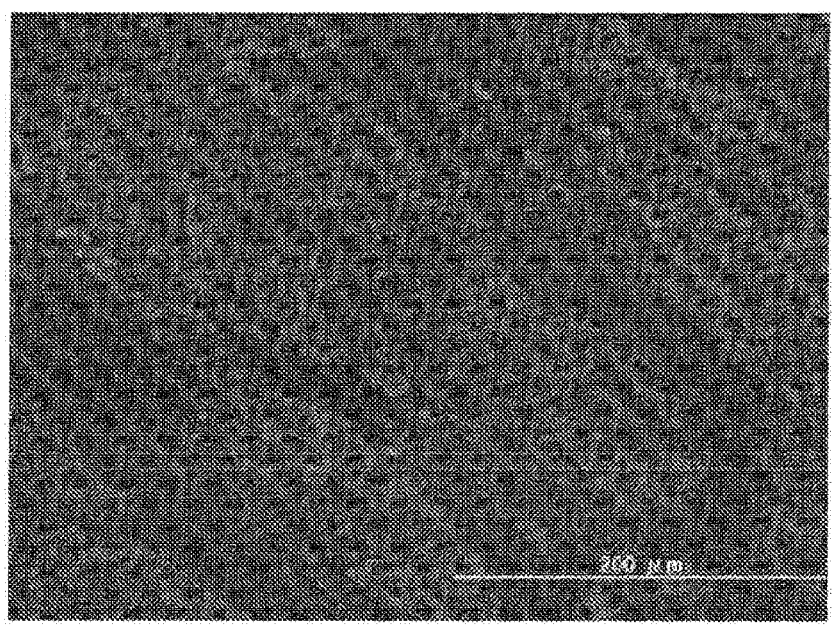
FIG. 4 is a diagram showing an example of a fluorescent image.

A fluorescent image is a microscopic image obtained by irradiating excitation light with a predetermined wavelength in the microscopic image obtaining apparatus 1A on the tissue slice stained using staining reagent including a nanoparticle including a fluorescent substance which specifically bonds with a certain biological substance and/or which bonds with reactive biological substance recognition site (hereinafter called fluorescent substance included nanoparticle) so that the fluorescent substance included nanoparticle emits light (fluorescence), and forming an image with the fluorescence to capture the image. In other words, the fluorescence which appears in the fluorescent image shows expression of the certain biological substance corresponding to the biological substance recognition site in the tissue slice. FIG. 4 shows an example of a fluorescent image.

<Obtaining Fluorescent Image>

Here, the method of obtaining the fluorescent image is described in detail including the description of the staining reagent used when obtaining the fluorescent image (fluorescent substance included nanoparticle), staining method of the tissue slice with the staining reagent, etc.

[Fluorescent Substance]

Examples of the fluorescent substance used in the staining reagent to obtain the fluorescent image include, fluorescent organic dye and quantum dot (semiconductor particle). Preferably, the substance shows an emission of visible rays to near infrared rays with a wavelength within the range of 400 to 1100 nm when excited by ultraviolet rays to near infrared rays with a wavelength within the range of 200 to 700 nm.

Examples of fluorescent organic dye include, fluorescein type dye molecule, rhodamine type dye molecule, Alexa Fluor (Invitrogen) type dye molecule, BODIPY (Invitrogen) type dye molecule, cascade type dye molecule, coumarin type dye molecule, eosin type dye molecule, NBD type dye molecule, pyrene type dye molecule, Texas Red type dye molecule, cyanine type dye molecule, and the like.

Specific examples include, 5-carboxy-fluorescein, 6-carboxy-fluorescein, 5,6-dicarboxy-fluorescein, 6-carboxy-2', 4, 4', 5',7, 7'-hexachlorofluorescein, 6-carboxy-2', 4, 7, 7'-tetrachlorofluorescein, 6-carboxy-4', 5'-dichloro-2', 7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above, Invitrogen), methoxycoumalin, eosin, NBD, pyrene, Cy5, Cy5.5, Cy7, etc. The above can be used alone or by mixing a plurality of types.

Examples of quantum dots which can be used include quantum dots including the following as the component, II-VI compounds, III-V compounds or IV element (also called, "II-VI quantum dot", "III-V quantum dot", "IV quantum dot", respectively). The above can be used alone or by mixing a plurality of types.

Specific examples include, but are not limited to, CdSe, CdS, CdTe, ZnSe, ZnS, ZnTe, InP, InN, InAs, InGaP, GaP, GaAs, Si, and Ge.

A quantum dot with the above quantum dot as the core and a shell provided on the core can also be used. As a method of expressing the quantum dot including a shell in the present specification, when the core is CdSe and the shell is ZnS, the above is expressed as CdSe/ZnS. Examples which can be used include, but are not limited to, CdSe/ZnS, CdS/ZnS, InP/ZnS, InGaP/ZnS, Si/SiO$_2$, Si/ZnS, Ge/GeO$_2$, Ge/ZnS, etc.

The quantum dot in which the surface is processed with organic polymer, etc. can be used as necessary. Examples include CdSe/ZnS with surface carboxy group (Invitrogen), CdSe/ZnS with surface amino group (Invitrogen), etc.

[Fluorescent Substance Included Nanoparticle]

The fluorescent substance included nanoparticle of the present invention is a nanoparticle with the fluorescent substance dispersed inside, and the fluorescent substance and the nanoparticle itself can be chemically bonded or not bonded.

The material composing the nanoparticle is not limited and examples include polystyrene, polyactate, silica, and the like.

The fluorescent substance included nanoparticle used in the present embodiment can be made by well-known methods. For example, a silica nanoparticle including fluorescent organic dye can be synthesized by referring to synthesizing an FTIC included silica particle as described in Langmuir volume 8, page 2921 (1992). Various fluorescent organic dye included silica nanoparticles can be synthesized using a desired fluorescent organic dye instead of FITC.

The silica nanoparticle including the quantum dot can be synthesized by referring to synthesizing of the CdTe included silica nanoparticle as described in New Journal of Chemistry, Volume 33, page 561 (2009).

The polystyrene nanoparticle including the fluorescent organic dye can be made using the copolymerization method using the organic dye including polymerizable functional group as described in U.S. Pat. No. 4,326,008 (1982), and impregnating method of the fluorescent organic dye to the polystyrene nanoparticle as described in U.S. Pat. No. 5,326,692 (1992).

The polymer nanoparticle including the quantum dot can be made using the impregnating method of the quantum dot to the polystyrene nanoparticle as described in Nature Biotechnology Volume 19, page 631 (2001).

The average particle diameter of the fluorescent substance included nanoparticle used in the present embodiment is not limited, and the fluorescent substance included nanoparticle with an average particle diameter with about 30 to 800 nm can be used. The variation coefficient showing the variety of the particle diameter (=(typical deviation/average value)×100%) is not limited, and preferably, the value is 20% or less. The electronic microscopic picture is captured using the scanning electron microscope (SEM), and the cross sectional area of a sufficient number of particles is calculated. The diameter of the circle when each measurement value is to be the area of the circle is obtained as the particle diameter. According to the present embodiment, the calculated average of the particle diameter of 1000 particles is to be the average particle diameter. The variation coefficient is to be a value calculated from the particle diameter distribution of 1000 particles.

[Bonding of the Biological Substance Recognition Site and Fluorescent Substance Included Nanoparticle]

The biological substance recognition site of the present embodiment is a site which specifically bonds and/or reacts with the target biological substance. The target biological substance is not limited as long as there is a substance which specifically bonds with the target biological substance. Representative examples includes protein (peptide), nucleic acid (oligonucleotide, polynucleotide), antibody, etc. Therefore, examples of substances which bond with such target biological substance include, antibody which recognizes the protein as antigen, other protein which specifically bonds with the protein, nucleic acid including a base sequence which hybrids with the nucleic acid, and the like. Specific examples include, anti HER2 antibody which specifically bonds with the HER2 which is a protein on the surface of the cell, anti ER antibody which specifically bonds with the estrogen receptor (ER) on the cell nucleus, anti actin antibody which specifically bonds with the actin forming the cytoskeleton, and the like. Among the above, anti HER2 antibody and anti ER antibody bonded to the fluorescent substance included nanoparticle are preferable because the above can be used in selecting medication for breast cancer.

The form of bonding between the biological substance recognition site and the fluorescent substance included nanoparticle is not limited, and examples include, covalent bonding, ion bonding, hydrogen bonding, coordinate bonding, physical adsorption, chemical adsorption, etc. Preferably, bonding with strong bonding force such as covalent bonding is preferable for stability of bonding.

Moreover, there can be an organic molecule which connects the biological substance recognition site with the fluorescent substance included nanoparticle. For example, in order to suppress non-specific adsorption with the biological substance, a polyethyleneglycol chain can be used and SM (PEG)12 by Thermo Scientific can be used.

When the biological substance recognition site is bonded to the fluorescent substance included silica nanoparticle, the same process can be applied whether the fluorescent substance is the fluorescent organic dye or the quantum dot. For example, a silane coupling agent which is a compound widely used for bonding inorganic material and organic material can be used. The silane coupling agent is a compound including a alkoxysilyl group providing a silanol group with hydrolysis in one end of the molecule and a functional group such as carboxy group, amino group, epoxy group, aldehyde group, etc. in the other end, and bonds with the inorganic material through an oxygen atom of the silanol group. Specific examples include, mercaptopropyl triethoxysilane, glycidoxypropyl triethoxysilane, aminopropyl triethoxysilane, silane coupling agent including polyethylene glycol chain (for example, PEG-silane no. SIM6492.7 by Gelest), and the like. When the silane coupling agent can be used, two or more types can be used together.

Well-known methods can be used as the reaction method between the fluorescent organic dye including silica nanoparticle and the silane coupling agent. For example, the obtained fluorescent organic dye included silica nanoparticle can be dispersed in pure water, the aminopropyl triethoxysilane can be added and the above can be reacted in room temperature for 12 hours. After the reaction ends, by centrifugal separation or filtration, it is possible to obtain a fluorescent organic dye included silica nanoparticle modified with the aminopropyl group. Next, the amino group is reacted with the carboxy group in the antibody so that the antibody can bond with the fluorescent organic dye included silica nanoparticle through amide bonding. According to necessity, condensing agent such as EDC (1-Ethyl-3-[3-Dimethylaminopropyl]carbodiimide Hydrochloride: Pierce (Registered Trademark)) can also be used.

According to necessity, a linker compound including a portion which can directly bond with the fluorescent organic dye included silica nanoparticle modified with the organic molecule and a portion which can bond with the molecule target substance can be used. For example, when sulfo-SMCC (SUlfosuccinimidyl 4[N-maleimidomethyl]-cyclohexane-1-carboxylate:Pierce) which has a portion which selectively reacts with the amino group and a portion which selectively reacts with the mercapto group is used, the amino group of the fluorescent organic dye included silica nanoparticle modified with aminopropyl triethoxysilane and the mercapto group in the antibody are bonded, and with this, the fluorescent organic dye included silica nanoparticle bonded with the antibody is made.

When the biological substance recognition site is bonded to the fluorescent substance included polystyrene nanoparticle, even if the fluorescent substance is the fluorescent organic dye, the same process as the quantum dot can be applied. In other words, by impregnating the fluorescent organic dye and the quantum dot in the polystyrene nanoparticle with the functional group such as the amino group, etc., it is possible to obtain the fluorescent substance included polystyrene nanoparticle with the functional group, and then by using the EDC or the sulfo-SMCC, the fluorescent substance included polystyrene nanoparticle bonded with the antibody is made.

Examples of the antibody which recognizes the specific antigen include the following, M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, C-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, VIII factor related antigen, fassin, FSH, galectin-3, gastrin, GFAP, glucagon, glycophorin A, granzyme B, hCG, hGH, helicobacter pyroli, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, p63, PAX 5, PLAP, pneumocystis calini, podoplanin (D2-40), PGR, prolactin, PSA, prostatic acid phosphatase, Renal Cell Carcinoma, 5100, somatostatin, spectrin, synaptophysin, TAG-72, TdT, cycloglobulin, TSH, TTF-1, TRAcP, tryptase, villin, vimentin, WT1, Zap-70, and the like.

[Staining Method]

Below, a staining method of a tissue slice is described. The staining method described below is not limited to a pathological slice of tissue, and can be applied to staining cells.

The method of creating the slice to which the staining method described below can be applied is not limited, and the slice which is made by well-known methods can be used.

1) Removing Paraffin

A pathological slice is immersed in a container with xylene, and paraffin is removed. The temperature is not limited, and the processing can be performed at room temperature. Preferably, the immersing time is 3 minutes or more to 30 minutes or less. The xylene can be changed during the immersion as necessary.

Next, the pathological slice is immersed in a container with ethanol, and the xylene is removed. The temperature is not limited, and the processing can be performed at room temperature. Preferably, the immersing time is 3 minutes or more to 30 minutes or less. The ethanol can be changed during the immersion as necessary.

Next, the pathological slice is immersed in a container with water, and the ethanol is removed, The temperature is not limited, and the processing can be performed at room temperature. Preferably, the immersing time is 3 minutes or more to 30 minutes or less. The water can be changed during the immersion as necessary.

2) Activating Processing

Activating processing of the target biological substance is performed according to well-known methods. Although the activating conditions are not specifically set, examples of activating liquid that can be used include, 0.01M citric acid buffered solution (pH 6.0), 1m MEDTA solution (pH 8.0), 5% urea, 0.1M tris-hydrochloric acid buffered solution. Examples of the heating device that can be used include autoclave, microwave, pressure pan, water bath, etc. The temperature is not limited, and the processing can be performed at room temperature. The processing can be performed at a temperature of 50 to 130° C. and the amount of time that the processing is performed can be 5 to 30 minutes.

Next, the slice after activating processing is immersed in the container with PBS (Phosphate Buffered Saline), and cleaning is performed. The temperature is not limited, and the processing can be performed at room temperature. Preferably, the immersing time is 3 minutes or more to 30 minutes or less. The PBS can be changed during the immersion as necessary.

3) Stain Using Fluorescent Substance Included Nanoparticle Bonded with Biological Substance Recognition Site The PBS dispersion liquid of the fluorescent substance included nanoparticle bonded with the biological substance recognition site is placed on the pathological slice and reacted with the target biological substance. By changing the biological substance recognition site bonded with the fluorescent substance included nanoparticle, staining can be applied to various biological substances. When the fluorescent substance included nanoparticle bonded with plural types of biological substance recognition sites is used, the fluorescent substance included nanoparticle PBS dispersion liquid of each of the above can be mixed in advance, or the liquid can be sequentially placed on the pathological slice separately.

The temperature is not limited, and the processing can be performed at room temperature. Preferably, the reacting time is 30 minutes or more to 24 hours or less.

Preferably, a well-known blocking agent such as BSA included PBS, etc. is dropped before staining with the fluorescent substance included nanoparticle.

Next, the slice after staining is immersed in the container with PBS, and the unreacted fluorescent substance included nanoparticle is removed. The temperature is not limited, and the processing can be performed at room temperature. Preferably, the immersing time is 3 minutes or more to 30 minutes or less. The PBS can be changed during the immersion as necessary. A cover glass is placed on the slice to be sealed. A commercially available sealing agent can be used as necessary.

When HE staining is performed, the HE staining is performed before sealing with the cover glass.

[Obtaining Fluorescent Image]

The microscopic image obtaining apparatus 1A is used on the stained pathological slice to obtain the microscopic image (fluorescent image) with a wide field. In the microscopic image obtaining apparatus 1A, the excitation light source and the fluorescence detecting optical filter are selected corresponding to the absorption maximum wavelength and the fluorescent wavelength of the fluorescent substance used in the staining reagent.

Preferably, the field of the fluorescent image is 3 $mm^2$ or more, more preferably 30 $mm^2$ or more, and even more preferably 300 $mm^2$ or more.

<Relationship Between Fluorescent Bright Point and FISH Score>

Here, as described below, the applicants made a Cy5 included silica nanoparticle (hereinafter referred to as nanoparticle 1) as one embodiment, and an indicator material A bonded with an anti HER2 antibody against the nanoparticle 1. Moreover, a CdSe/ZnS included silica nanoparticle (hereinafter referred to as nanoparticle 2) is made and an indicator material B bonded with an anti HER2 antibody is made with a nanoparticle 2. By using the made indicator material A and B and the indicator material C and D as the comparison example, an adjacent slice of the human breast tissue in which the FISH score is measured in advance is used to perform immunostaining, a plurality of fluorescent images with different fields are obtained, and the fluorescent bright spot appearing in each fluorescent image is measured to perform an experiment of finding the relation with the FISH score.

[Synthesis of Fluorescent Substance Included Nanoparticle]

(Synthesis Example 1: Fluorescent Organic Dye Included Silica: Synthesis of Cy5 Included Silica Nanoparticle)

The Cy5 included silica nanoparticle (nanoparticle 1) is made by the method including the following steps of (1) to (5).

step (1): 1 mg (0.00126 mmol) of N-hydroxysuccinimideester derivative of Cy5 (GE healthcare) and 400 µL (1.796 mmol) of tetraethoxysilane are mixed.

step (2): 40 mL of ethanol and 10 mL of 14% aqueous ammonium are mixed.

step (3): The mixed liquid prepared in step (1) is added while stirring the mixed liquid made in step (2) at room temperature. The stirring continues for 12 hours from when the adding starts.

step (4): Centrifugal separation is performed on the reacted mixture at 10000 G for 60 minutes and the supernatant is removed.

step (5): Ethanol is added, precipitate is dispersed and centrifugal separation is performed again. Cleaning is performed using ethanol and pure water, one time each with the similar process.

The obtained nanoparticle 1 observed with the scanning electron microscope (SEM; Hitachi (registered trademark) S-800 type) has an average particle diameter of 110 nm, and a variation coefficient of 12%.

(Synthesis Example 2: Quantum Dot Included Silica: Synthesis of CdSe/ZnS Included Silica Nanoparticle with Emission Wavelength of 655 nm)

The CdSe/ZnS included silica nanoparticle (hereinafter referred to as nanoparticle 2) is made by the method including the following steps (1) to (5).

step (1): 10 μL of CdSe/ZnS decane dispersion liquid (Invitrogen, Qdot 655) and 40 μL of tetraethoxysilane are mixed.

step (2): 4 mL of ethanol and 1 mL of 14% aqueous ammonium are mixed.

step (3): The mixed liquid made in step (1) is added while stirring the mixed liquid made in step (2) at room temperature. The stirring continues for 12 hours from when the adding starts.

step (4): Centrifugal separation is performed on the reacted mixture at 10000 G for 60 minutes and the supernatant is removed.

step (5): Ethanol is added, precipitate is dispersed and centrifugal separation is performed again. Cleaning is performed using ethanol and pure water, one time each with the similar process.

The obtained nanoparticle 2 observed with the scanning electron microscope has an average particle diameter of 130 nm, and a variation coefficient of 13%.

[Bonding Antibody to Fluorescent Substance Included Silica Nanoparticle]

The antibody is bonded to the fluorescent substance included silica nanoparticle according to the method including the following steps (1) to (12). Here, an example using the nanoparticle 1 is shown, however, the same applies to the nanoparticle 2.

step (1): 1 mg of the nanoparticle 1 is dispersed in 5 mL of pure water. Next, 100 μL of aminopropyltriethoxysilane aqueous dispersion liquid is added and the stirring continues for 12 hours at room temperature.

step (2): Centrifugal separation is performed on the reacted mixture at 10000 G for 60 minutes and the supernatant is removed.

step (3): Ethanol is added, precipitate is dispersed and centrifugal separation is performed again. Cleaning is performed using ethanol and pure water, one time each with the similar process.

When the FT-IR measurement of the obtained silica nanoparticle modified with the amino group is performed, adsorption due to the amino group can be observed, and it is possible to confirm that the silica nanoparticle is modified with the amino group.

step (4): the silica nanoparticle modified with the amino group obtained in step (3) is adjusted to 3 nM using the PBS including 2 mM of EDTA (ethylenediaminetetraacetic acid).

step (5): SM(PEG) 12 (Thermoscientific, succinimidyl-[(N-maleomidopropionamid)-dodecaethyleneglycol]ester) is mixed in the solution adjusted in step (4) so that the final concentration is 10 mM and the above is reacted for 1 hour.

step (6): Centrifugal separation is performed on the reacted mixture at 10000 G for 60 minutes and the supernatant is removed.

step (7): PBS including 2 mM of EDTA is added, precipitate is dispersed and centrifugal separation is performed again. Cleaning by similar processing is performed 3 times. Finally, 50 μL of PBS is used to disperse again.

step (8): 100 μg of the anti HER2 antibody is dissolved in 100 μL of the PBS, 1M dithiothreitol (DTT) is added and the above is reacted for 30 minutes.

step (9): The excessive DTT is removed from the reacted mixture with the gel filter column and a reduced anti HER2 antibody solution is obtained.

step (10): The particle dispersion liquid obtained in step (7) with the nanoparticle 1 as the starting material is mixed with the reduced anti HER2 antibody solution obtained in step (9) in the PBS and the above is reacted for 1 hour.

step (11): 4 μL of 10 mM mercaptoethanol is added and the reaction is terminated.

step (12): Centrifugal separation is performed on the reacted mixture at 10000 G for 60 minutes and the supernatant is removed. Then, PBS including 2 mM of EDTA is added, the precipitate is dispersed and centrifugal separation is performed again. Cleaning by similar processing is performed 3 times. Finally, 500 μL of PBS is used to disperse again to obtain the fluorescent substance included silica nanoparticle bonded with the anti HER2 antibody.

The fluorescent substance included silica nanoparticle bonded with the anti HER2 antibody obtained with the nanoparticle 1 as the starting material is to be the indicator material A, and the fluorescent substance included silica nanoparticle bonded with the anti HER2 antibody obtained with the nanoparticle 2 as the starting material is to be the indicator material B.

As the comparison example, the anti HER2 antibody is bonded to the Cy5 to obtain reduced anti HER antibody solution (indicator material D). Similarly, the indicator material C is made by bonding the anti HER2 antibody to the CdSe.

[Staining Tissue Using Fluorescent Substance Included Nanoparticle]

According to the method including the following steps (1) to (10), the made antibody bonded indicator materials A to D are used to perform immunostaining using adjacent slices of human breast tissue with which the FISH score is measured in advance. A tissue array slide (CB-A712) of Cosmobio is used as the stain slice. 24 slices with a FISH score from 1 to 9 are used.

step (1): The pathological slice is immersed in a container with xylene for 30 minutes. The xylene is changed 3 times during the process.

step (2): The pathological slice is immersed in a container with ethanol for 30 minutes. The ethanol is changed 3 times during the process.

step (3): The pathological slice is immersed in a container with water for 30 minutes. The water is changed 3 times during the process.

step (4): The pathological slice is immersed in 10 mM citric acid buffered solution (pH 6.0) for 30 minutes.

step (5): The autoclave processing is performed for 10 minutes at 121 degrees.

step (6): A slice after autoclave processing is immersed in a container with PBS for 30 minutes.

step (7): 1% BSA included PBS is placed on the tissue and left as is for 1 hour.

step (8): The indicator materials A to D bonded with anti HER2 antibody which are diluted by the 1% BSA included PBS to 0.05 nM are placed on each tissue slice and left as is for 3 hours.

step (9): Each slice after staining is immersed in a container with PBS for 30 minutes.

step (10): After dropping Aquatex by Merck Chemical, the cover glass is placed to be sealed.

[Experiment Results]

A plurality of fluorescent images are obtained changing the field (observation area) of the tissue slice stained using each indicator material A to D, and the number of fluorescent bright points (bright point number) is measured from each fluorescent image with the image analysis software.

An upright microscope Axio Imager M2 manufactured by Carl Zeiss is used as the microscope. An objective lens is set to 20 times, an excitation light with a wavelength of 630 to 670 nm is irradiated, fluorescence emitted from a tissue slice is imaged, a fluorescent image (image data) is obtained with the camera attached to the microscope (monochrome), and the bright point number is measured with the image analysis software. Regarding the camera, the pixel size is 6.4 μm×6.4 μm, the vertical number of pixels is 1040 pixels, and the horizontal number of pixels is 1388 pixels (imaging region 8.9 mm×6.7 mm).

Regarding each indicator material A to D, the correlation coefficient R between the measured bright point number and the FISH score is calculated for each field. The FISH score corresponds to the overexpression level of the HER2 gene, and the higher the value of the FISH score is, this shows that the overexpression level of the HER2 gene is high.

Figure 5:
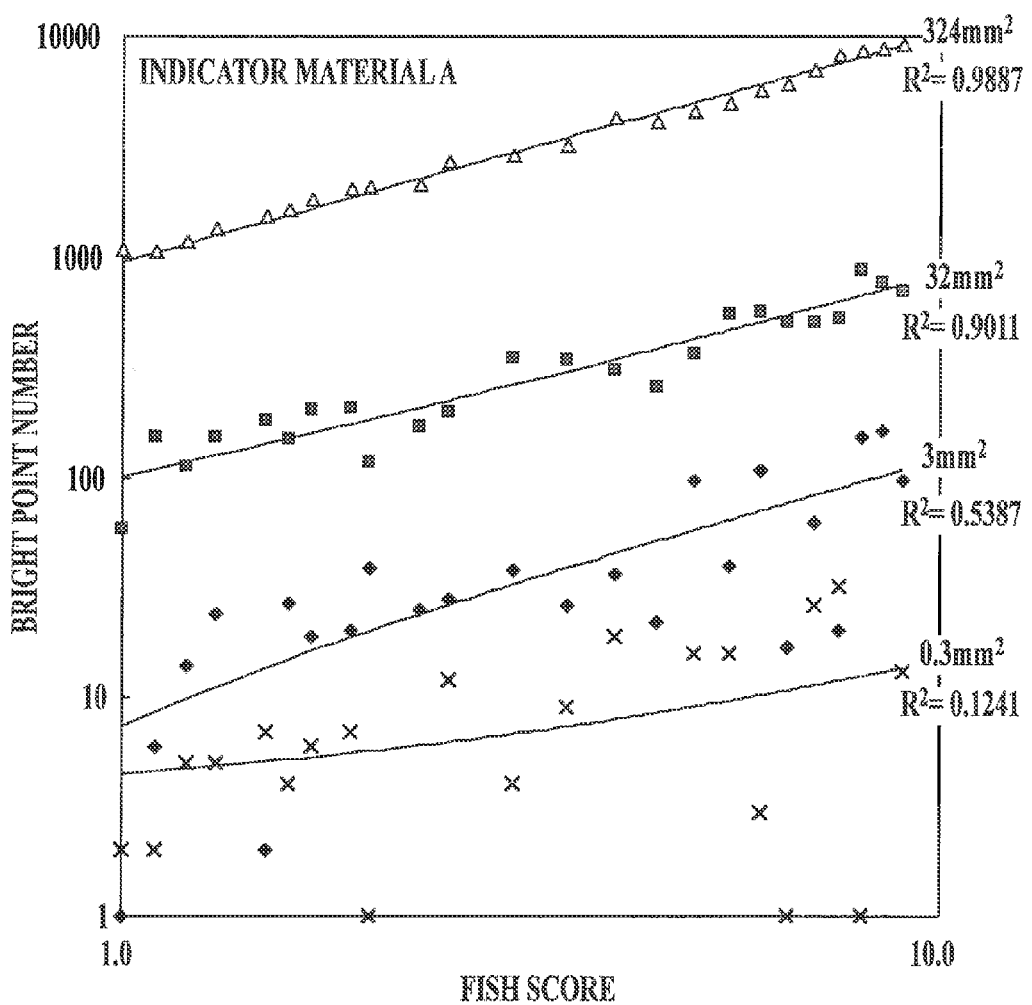
FIG. 5 is a diagram showing a relation between a bright point number and a FISH score when an indicator material A is used.

FIG. 5 is a diagram showing a relation between the bright point number measured from the fluorescent images with a plurality of different fields (0.3 mm$^2$, 3 mm$^2$, 32 mm$^2$, 324 mm$^2$) and the FISH score when the indicator material A (Cy5 included indicator material) is used. The value of R$^2$ shown in the diagram is a square value of the correlation coefficient between the bright point number and the FISH score.

Figure 6:
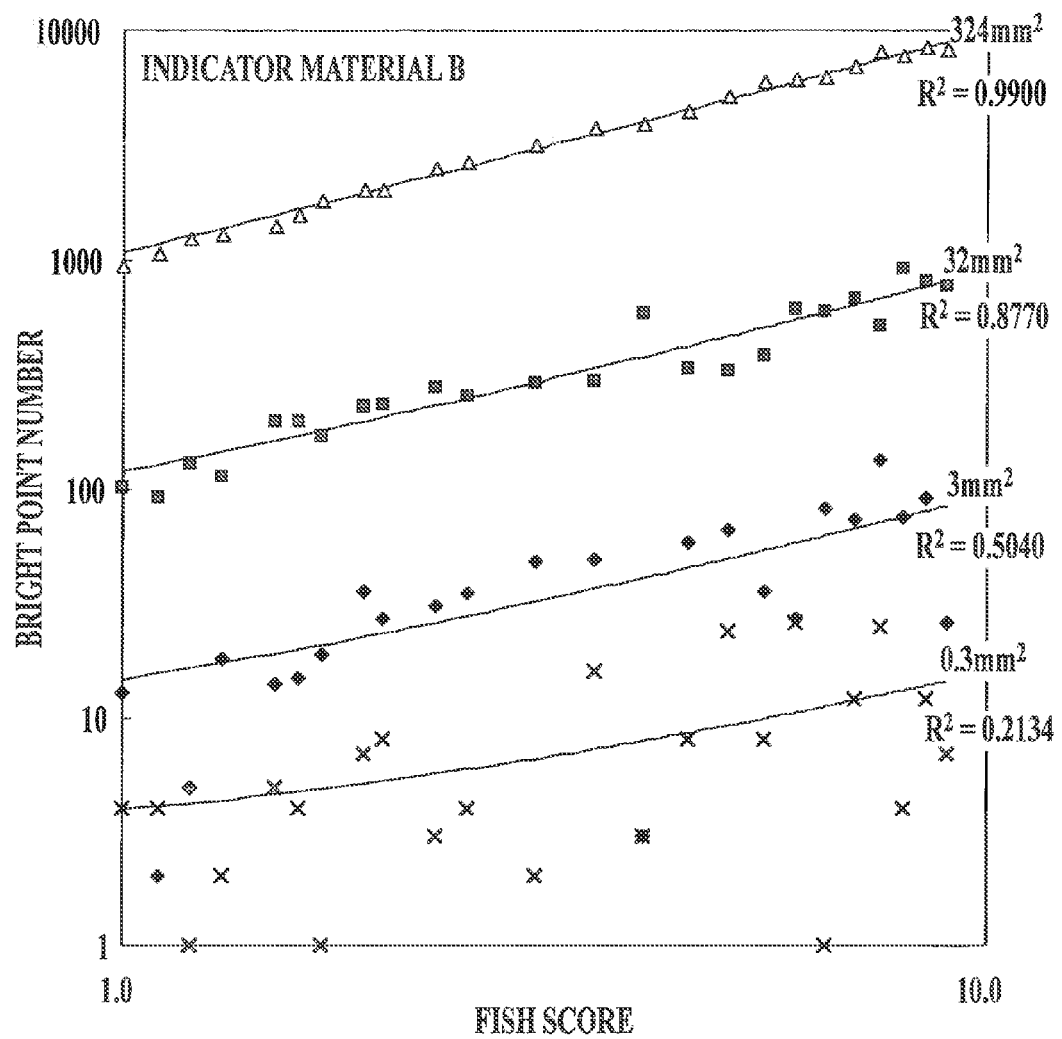
FIG. 6 is a diagram showing a relation between a bright point number and a FISH score when an indicator material B is used.

FIG. 6 is a diagram showing a relation between the bright point number measured from the fluorescent images with a plurality of different fields (0.3 mm$^2$, 3 mm$^2$, 32 mm$^2$, 324 mm$^2$) and the FISH score when the indicator material B (CdSe included indicator material) is used.

Figure 7:
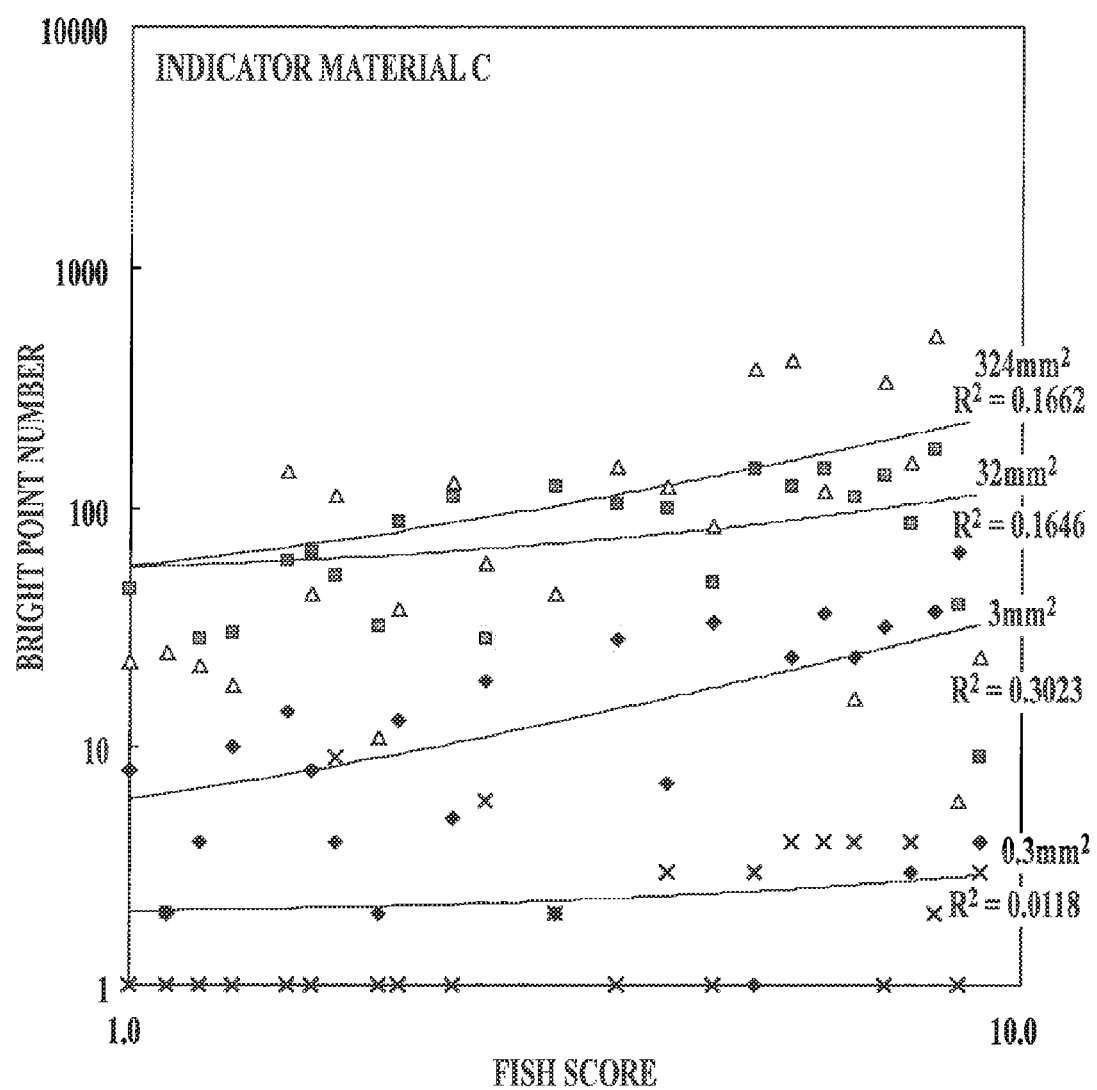
FIG. 7 is a diagram showing a relation between a bright point number and a FISH score when an indicator material C is used.

FIG. 7 is a diagram showing a relation between the bright point number measured from the fluorescent images with a plurality of different fields (0.3 mm$^2$, 3 mm$^2$, 32 mm$^2$, 324 mm$^2$) and the FISH score when the indicator material C (CdSe) is used.

Figure 8:
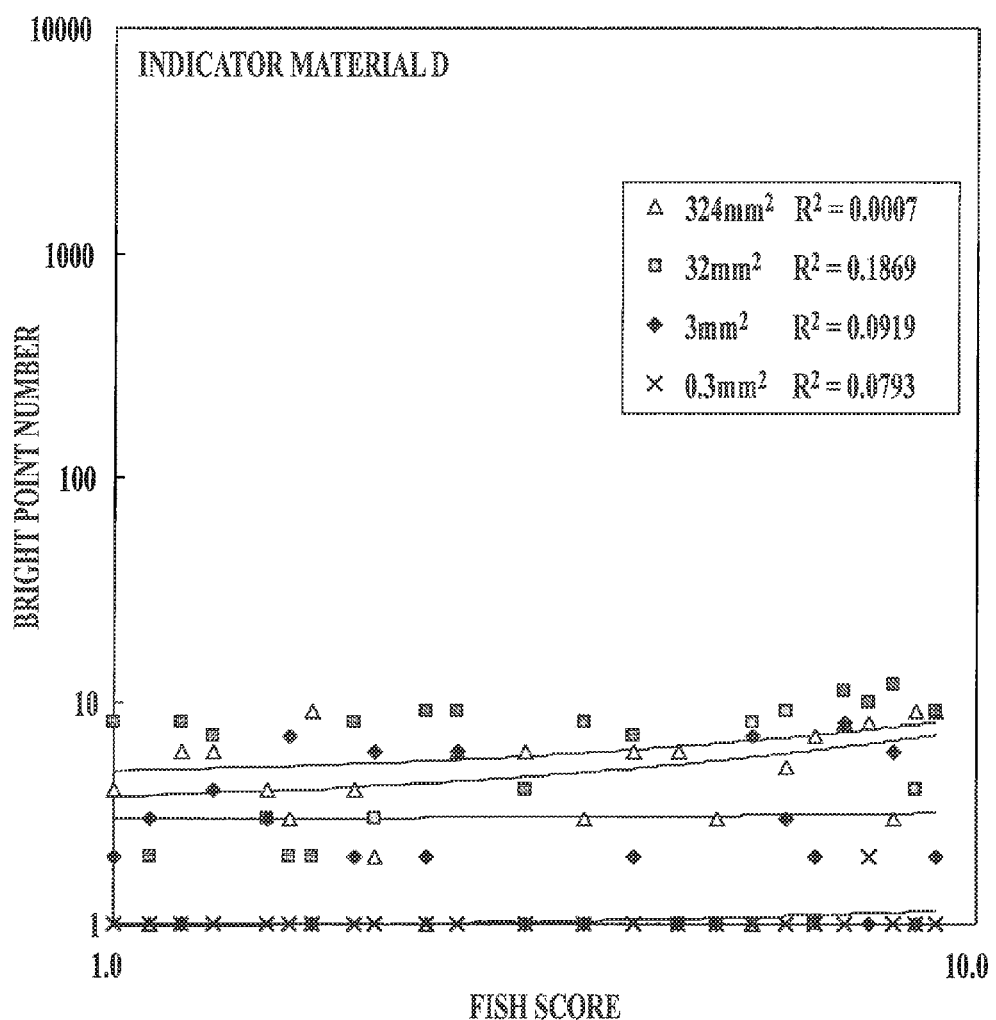
FIG. 8 is a diagram showing a relation between a bright point number and a FISH score when an indicator material D is used.

FIG. 8 is a diagram showing a relation between the bright point number measured from the fluorescent images with a plurality of different fields (0.3 mm$^2$, 3 mm$^2$, 32 mm$^2$, 324 mm$^2$) and the FISH score when the indicator material D (Cy5) is used.

Figure 9:
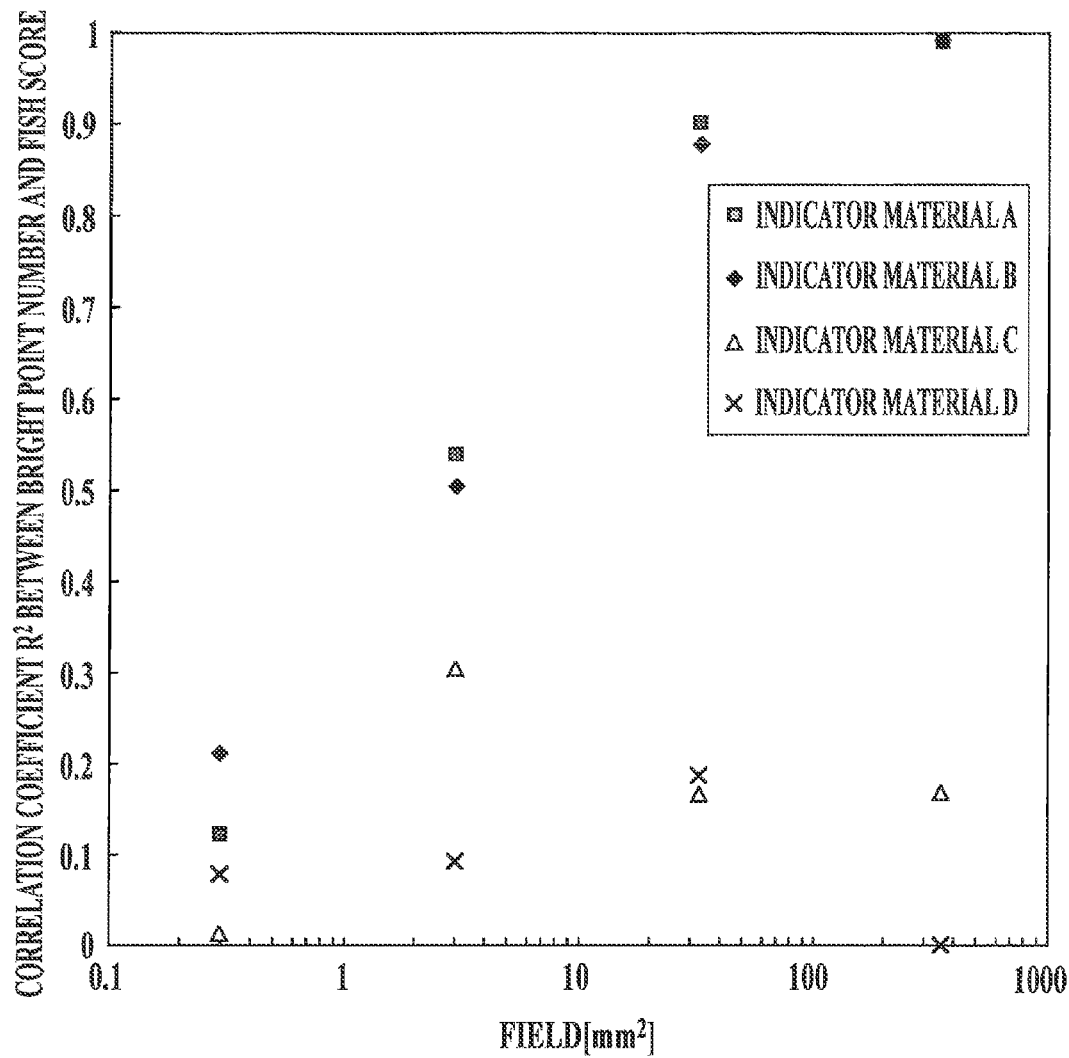
FIG. 9 is a diagram showing a square value of a correlation coefficient between a bright point number and a FISH score measured from a microscopic image of each field in each indicator material A to D.

Table 1 and FIG. 9 show a square value (R$^2$) of the correlation coefficient between the bright point number measured from the fluorescent image of each field (observation area) and the FISH score for each indicator material A to D.

TABLE 1

| INDICATOR MATERIAL | FIELD (OBSERVATION AREA) | CORRELATION COEFFICIENT R$^2$ BETWEEN BRIGHT POINT NUMBER AND FISH SCORE |
|---|---|---|
| INDICATOR MATERIAL A | 0.3 mm$^2$ | 0.1241 |
|  | 3 mm$^2$ | 0.5387 |
|  | 32 mm$^2$ | 0.9011 |
|  | 324 mm$^2$ | 0.9887 |
| INDICATOR MATERIAL B | 0.3 mm$^2$ | 0.2134 |
|  | 3 mm$^2$ | 0.5040 |
|  | 32 mm$^2$ | 0.8770 |
|  | 324 mm$^2$ | 0.9900 |
| INDICATOR MATERIAL C | 0.3 mm$^2$ | 0.0118 |
|  | 3 mm$^2$ | 0.3023 |
|  | 32 mm$^2$ | 0.1646 |
|  | 324 mm$^2$ | 0.1662 |
| INDICATOR MATERIAL D | 0.3 mm$^2$ | 0.0793 |
|  | 3 mm$^2$ | 0.0919 |
|  | 32 mm$^2$ | 0.1869 |
|  | 324 mm$^2$ | 0.0007 |

When the indicator material A is used to stain the tissue slice and the bright point number is measured from the fluorescent image with a field of 0.3 mm$^2$, the square value (R$^2$) of the correlation coefficient between the bright point number and the FISH score is 0.1241 and no correlation can be seen between the bright point number and the FISH score. It is assumed this is because the field of 0.3 mm2 is too small and the variation is large.

When the indicator material A is used to stain the tissue slice and the bright point number is measured from the fluorescent image with a field of 3 mm$^2$, the square value (R$^2$) of the correlation coefficient between the bright point number and the FISH score is 0.5387. When converted to the correlation coefficient R, this value is about 0.734, and it can be said that there is a strong correlation between the bright point number and the FISH score.

When the indicator material A is used to stain the tissue slice and the bright point number is measured from the fluorescent image with a field of 32 mm$^2$, the square value (R$^2$) of the correlation coefficient between the bright point number and the FISH score is 0.9011. It can be said that the correlation is stronger when the field is 32 mm$^2$ compared to when the field is 3 mm$^2$.

When the indicator material A is used to stain the tissue slice and the bright point number is measured from the fluorescent image with a field of 324 mm$^2$, the square value (R$^2$) of the correlation coefficient between the bright point number and the FISH score is 0.9887. It can be said that the correlation is stronger when the field is 324 mm$^2$ compared to when the field is 32 mm$^2$.

Similarly, when the indicator material B is used, in a field equal to or larger than 3 mm$^2$, it is found that there is correlation between the bright point number and the FISH score, and the correlation coefficient becomes larger as the field becomes larger.

From the result of using the indicator materials A and B, it is found that the square value (R2) of the correlation coefficient between the bright point number and the FISH score is close enough to 1 when the field is 324 mm$^2$.

On the other hand, when the tissue slice is stained using the indicator material C or indicator material D, correlation cannot be seen between the bright point number and the FISH score.

Moreover, even if the focus of the microscope is slightly moved to the upper portion or the lower portion in the thickness (normally, a few μm) of the observation target tissue slice, a significant difference in the situation cannot be seen.

From the above results, when the tissue slice using the indicator materials A and B is observed with a large field, it is found that the correlation between the bright point number and the FISH score is good, and the expression level of the HER2 gene can be evaluated based on the bright point number. In other words, instead of using a troublesome method such as the FISH method, by staining the tissue slice with the stain reagent of the fluorescent substance included nanoparticle bonded with the biological substance recognition site which recognizes a specific biological substance, and measuring the bright point number from the image with the field of 3 mm$^2$ or larger obtained by imaging the above enlarged with the microscope and capturing the image, the expression level of the specific biological substance can be evaluated. The above is effective as a method to replace the FISH method.

The indicator materials A and B use particles including a fluorescent substance, and has a larger brightness compared to the indicator materials C and D which use the fluorescent substance as a simple substance. Therefore, each one of the bright points can be identified easily from the image, and the bright point number can be calculated accurately.

<Operation of Pathological Diagnosis Assistance System 100>

Below, the operation of obtaining the above described fluorescent image and the bright field image and performing analysis in the pathological diagnosis assistance system 100 is described. In the description below, the observation target is the tissue slice stained using the stain reagent including the fluorescent substance included nanoparticle bonded with the biological substance recognition site which recognizes a specific protein (Here, HER 2 protein in breast cancer tissue. Hereinafter referred to as specific protein). However, the observation target is not limited to the above.

First, the bright field image and the fluorescent image are obtained with the microscopic image obtaining apparatus 1A by steps (a1) to (a5).

(a1) The operator places a slide on which the tissue slice stained with the stain reagent including the fluorescent substance included nanoparticle bonded with the biological substance recognition site which recognizes the specific protein as the fluorescent indicator material and the HE agent on the slide fixing stage of the microscopic image obtaining apparatus 1A.

(a2) The bright field unit is set, the capturing magnification and focus are adjusted, and the region of the observation target on the tissue is positioned in the field.

(a3) Capturing is performed with the capturing unit to generate the image data of the bright field image, and the image data is transmitted to the image processor 2A.

(a4) The unit is changed to the fluorescent unit.

(a5) Capturing is performed with the capturing unit without changing the field and the capturing magnification to generate the image data of the fluorescent image, and the image data is transmitted to the image processor 2A.

As described above, in the microscopic image obtaining apparatus 1A, the bright field image and the fluorescent image are obtained from the slide with the same tissue slice with the same capturing magnification within the same range (same field). Therefore, the same coordinate position in the bright field image and the fluorescent image show the same position in the tissue slice, and positions do not need to be matched between the two images.

According to consideration by the inventors, etc. of the present application, when the HE staining and the staining by the fluorescent substance included nanoparticle are performed at the same time, if the fluorescent bright point of the fluorescent substance included nanoparticle has a luminescence amount difference of 10% (1.1 times) or more from the autofluorescence of the tissue and the light emission of the eosin (background), the automatic processing of detecting the fluorescent bright point from the microscopic image (fluorescent image) is possible under any of the processing systems of 8 bits (0 to 255 tones) and 12 bits (0 to 4095 tones). When only the staining by the fluorescent substance included nanoparticle is performed, if the fluorescent substance included nanoparticle has a luminescence amount difference of 10% (1.1 times) or more from the autofluorescence of the tissue, the automatic processing of detecting the fluorescent bright point is possible under any of the processing systems of 8 bits (0 to 255 tones) and 12 bits (0 to 4095 tones). Therefore, preferably, the excitation light wavelength in the fluorescent unit is selected from within the range of 560 to 630 nm, and the fluorescent substance used emits fluorescence including a peak within the range of 580 to 690 nm, more preferably within the range of 600 to 630 nm by the excitation light. If the fluorescent substance includes a peak within the above range, when the excitation light within the above range is selected, it is possible to secure the luminescence difference between the autofluorescence of the tissue including light emission of eosin and fluorescence from the fluorescent substance included nanoparticle, and with this, it is possible to surely distinguish and recognize the difference between the above (luminescence difference of the above being 10% (1.1 times) or more).

When the HE staining is not performed at the same time, the autofluorescence of the tissue is very weak, and therefore, even if the range of the wavelength of the excitation light is not limited within the typical range of 200 nm to 700 nm, it is possible to secure the luminescence difference between the autofluorescence and fluorescence from the fluorescent substance included nanoparticle, and with this, it is possible to surely distinguish and recognize the difference between the above (luminescence difference of the above being 10% (1.1 times) or more).

In the image processor 2A, image analysis processing A is performed based on the bright field image and the fluorescent image.

Figure 10:
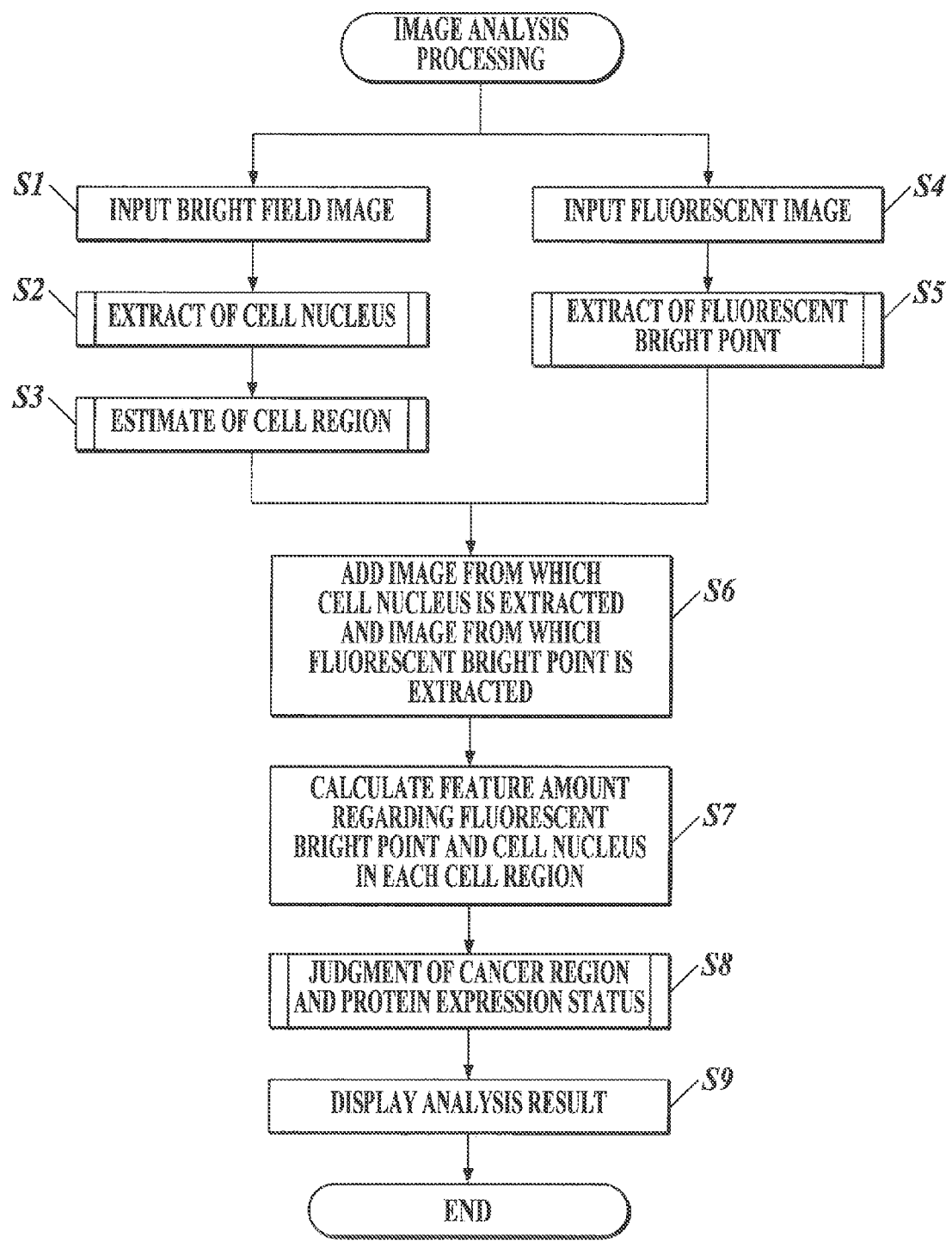
FIG. 10 is a flowchart showing image analysis processing performed by a control section of FIG. 2.

FIG. 10 shows a flowchart of the image analysis processing A in the image processor 2A. The image analysis processing shown in FIG. 10 is performed by the control section 21 in coordination with the program stored in the storage section 25.

First, when the bright field image is input from the microscopic image obtaining apparatus 1A through the communication I/F 24 (step S1), the region of the cell nucleus is extracted from the bright field image (step S2).

Figure 11:
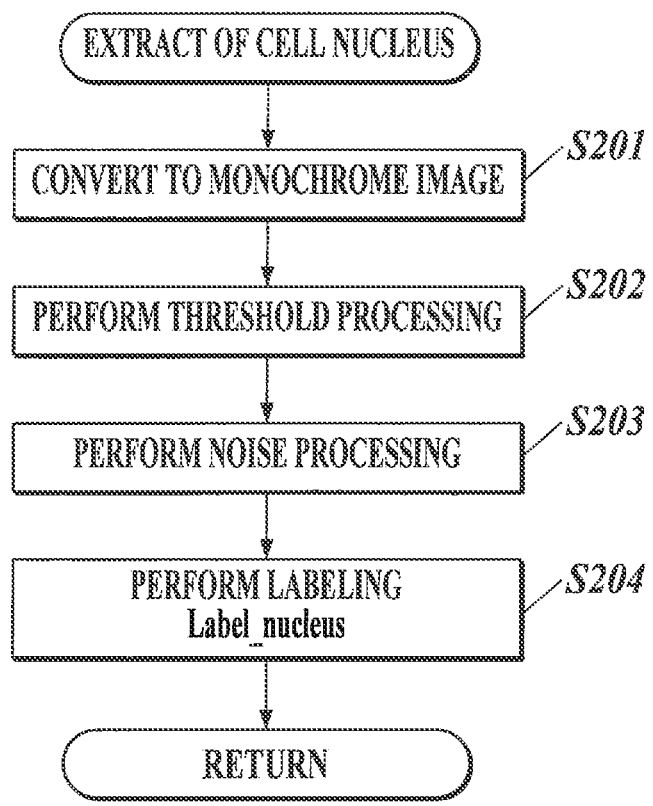
FIG. 11 is a flowchart showing details of processing of step S2 of FIG. 10.

FIG. 11 shows a detailed flow of the processing of step S2. The processing of step S2 is performed by the control section 21 in coordination with the program stored in the storage section 25.

In step S2, first, the conversion of the bright field image to the monochrome image is performed (step S301).

Figure 12:
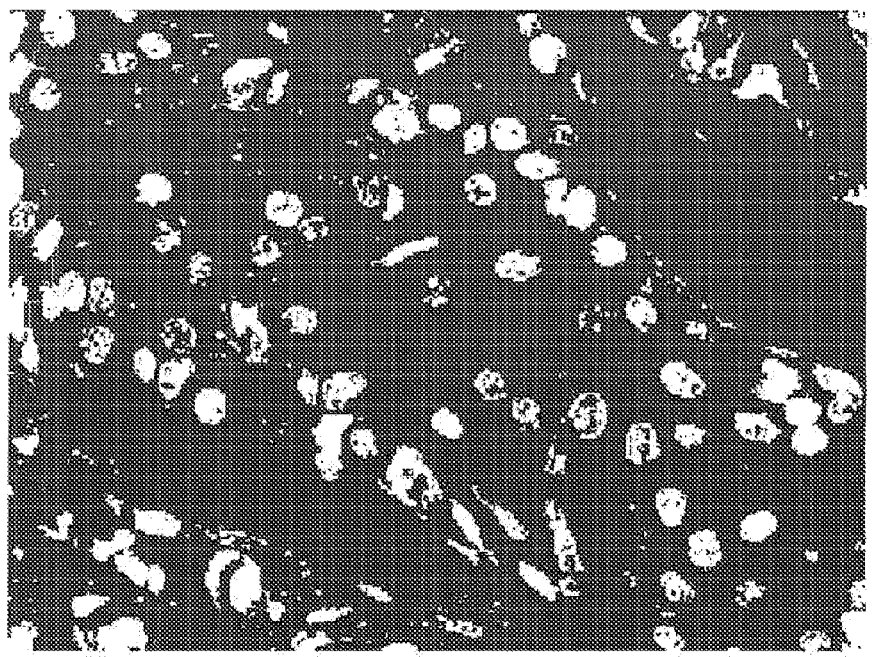
FIG. 12 is a diagram showing an example of a binary image after threshold processing.

Then, threshold processing is performed on the monochrome image using a threshold determined in advance, and each value of the pixel is binarized (step S202). FIG. 12 shows an example of a binary image after threshold processing.

Figure 13:
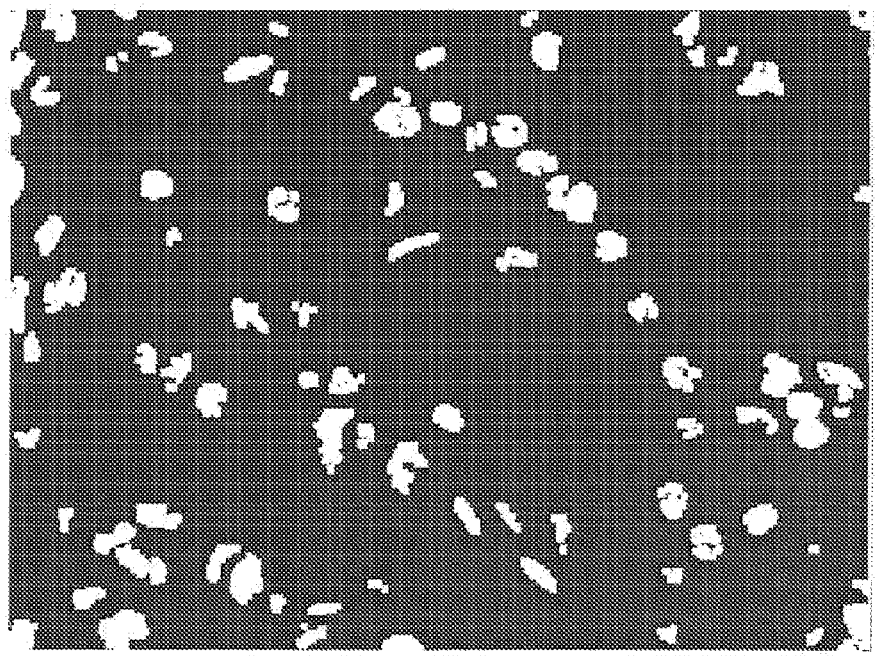
FIG. 13 is a diagram showing an example of a binary image after noise processing.

Next, noise processing is performed (step S203). Specifically, the noise processing can be performed by performing closing processing on the binary image. The closing processing is processing of performing dilation processing and then erosion processing the same number of times. The dilation processing is processing of replacing the target pixel with a white pixel when any of the pixels within the range of n×n pixels (n is an integer of 2 or more) from the target pixel is white. The erosion processing is processing of replacing the target pixel with a black pixel when any of the pixels within the range of n×n pixels from the target pixel is black. Small regions such as noise can be removed with the closing processing. FIG. 13 shows an example of an image after noise processing. As shown in FIG. 13, after the noise processing, an image (cell nucleus image) with the cell nucleus extracted can be obtained.

Next, labeling processing is performed on the image after noise processing, and a label Label_nucleus is attached to each extracted cell nucleus (step S204). The labeling processing is processing of attaching the same label (number) to the connecting pixels to identify the object in the image. According to the labeling processing, each cell nucleus can be identified from the image after noise processing and a label can be attached.

In order to distinguish the above from the label number in extracting the fluorescent bright point as described later, when the maximum value which the computer can hold is MAX, and the number of times of labeling up to the present point is Label_temp, MAX-Label_temp is attached to the new cell nucleus as the label Label_nucleus. For example, when a label is attached to the 101-st cell nucleus, since Label_temp=100, if MAX=65536, 65436 is attached as the Label_nucleus. After labeling processing the processing advances to step S3 of FIG. 10.

In step S3 of FIG. 10, the cell region in the bright field image is estimated based on the region of the cell nucleus extracted in step S2 (step S3). Here, a circular region which has a radius r with a centroid of the region of each extracted cell nucleus as the center is set. When the set circular region does not overlap with other circular regions, the set circular region is estimated to be a cell region including one cell (see FIG. 20A). When a plurality of the set circular regions overlap on one another, the region surrounded by the outer circumference of the plurality of overlapped circular regions is estimated to be a cell region including a plurality of cells (see FIG. 20B). Here, in the periphery of the cell membrane of the cancerous cell, overexpression of the specific protein can be seen. The radius r is to be a size which surely includes the specific protein expressed in the cell membrane periphery.

In the present embodiment, the region set from the centroid of each cell nucleus in order to estimate the cell region is described as the circular region. However, the region is to be a region from the centroid of each cell nucleus to the expression region of the specific protein in the cell membrane periphery, and the shape is not limited.

The radius r changes according to the capturing magnification of the input bright field image. In step S3, the cell nucleus size S_base which is to be a predetermined basis is compared with an average cell nucleus size S_ave_in of the normal cell nucleus obtained from the bright field image to determine the capturing magnification of the input bright field image, and the radius r is determined based on the determined capturing magnification. Since the cell nucleus of the cancerous cell is large, a size of a normal cell nucleus which is estimated to be a cell which is not cancerous is used as the basis cell nucleus size and the average cell nucleus size for determining the capturing magnification.

Figure 14:
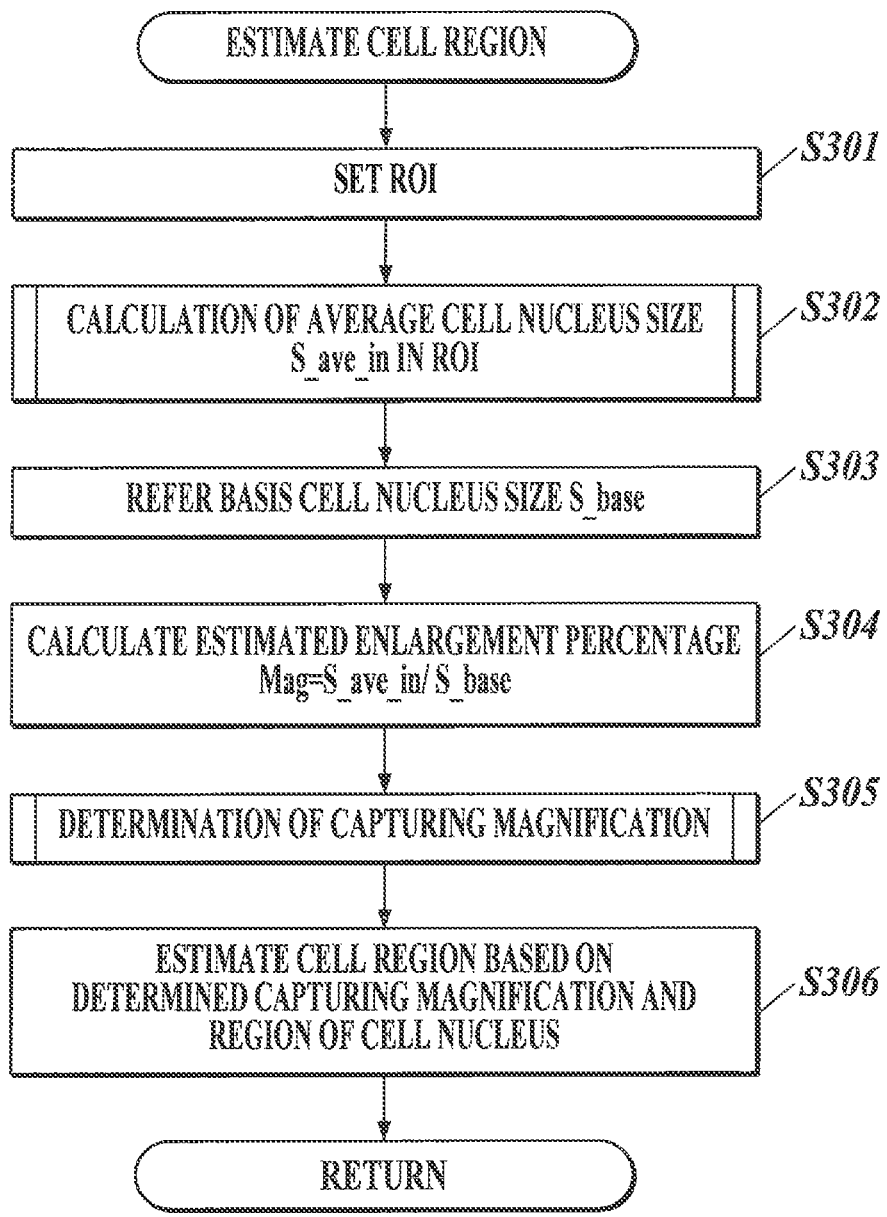
FIG. 14 is a flowchart showing details of processing of step S3 of FIG. 10.

FIG. 14 shows a detailed flow of the processing of step S3. The processing of step S3 is performed by the control section 21 in coordination with the program stored in the storage section 25.

Figure 15:
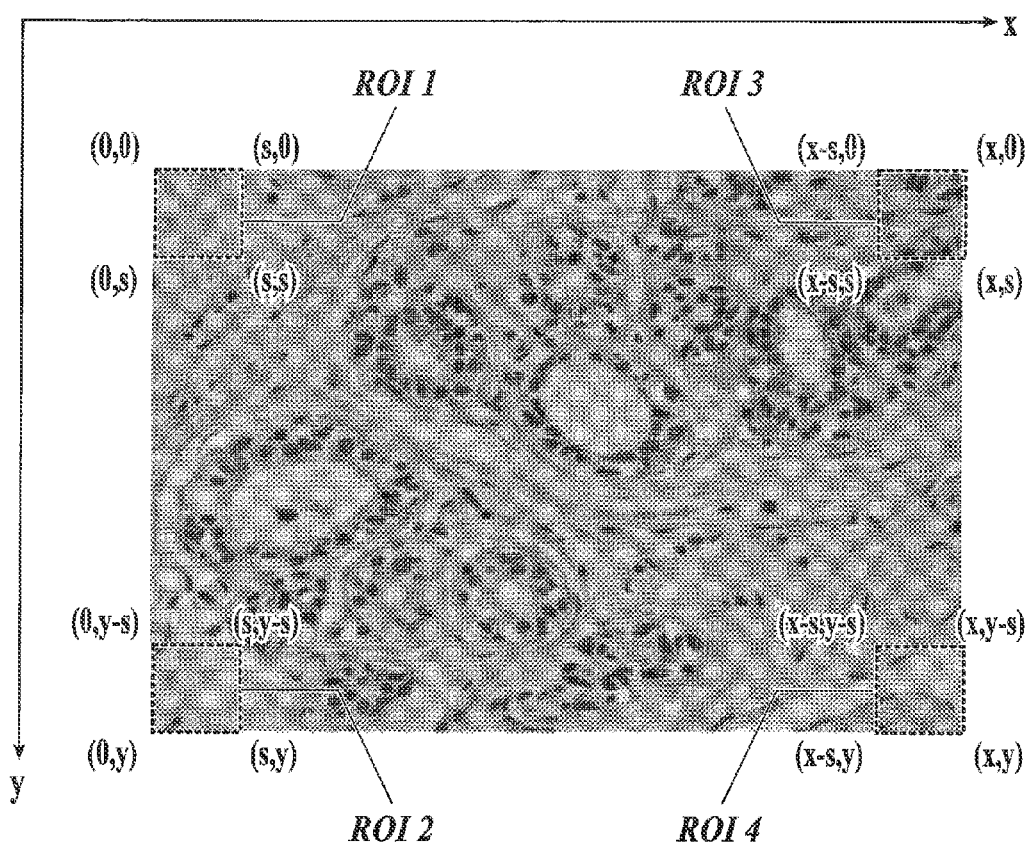
FIG. 15 is a diagrams showing an example of ROI set in step S301 of FIG. 14.

First, the ROI for determining the capturing magnification is set in the bright field image (step S301). Here, the bright field image obtained in the microscopic image obtaining apparatus 1A is an image in which a tissue slice of the observation target is enlarged to a certain capturing magnification. In step S301, an ROI for determining the capturing magnification is set. FIG. 15 shows an example of an ROI set in step S301. As shown in FIG. 15, for example, a rectangular region with s pixels×pixels in four corners of the bright field image is set as the ROI 1 to ROI 4. Usually, the bright field image is captured by matching the region on the slice where the physician gives attention to with the center, and therefore, there is a high possibility that the center portion of the image includes the cancerous cell. Therefore, the four corners of the image are set as the ROI.

Next, the average cell nucleus size S_ave_in in each set ROI region is calculated (step S302).

Figure 16:
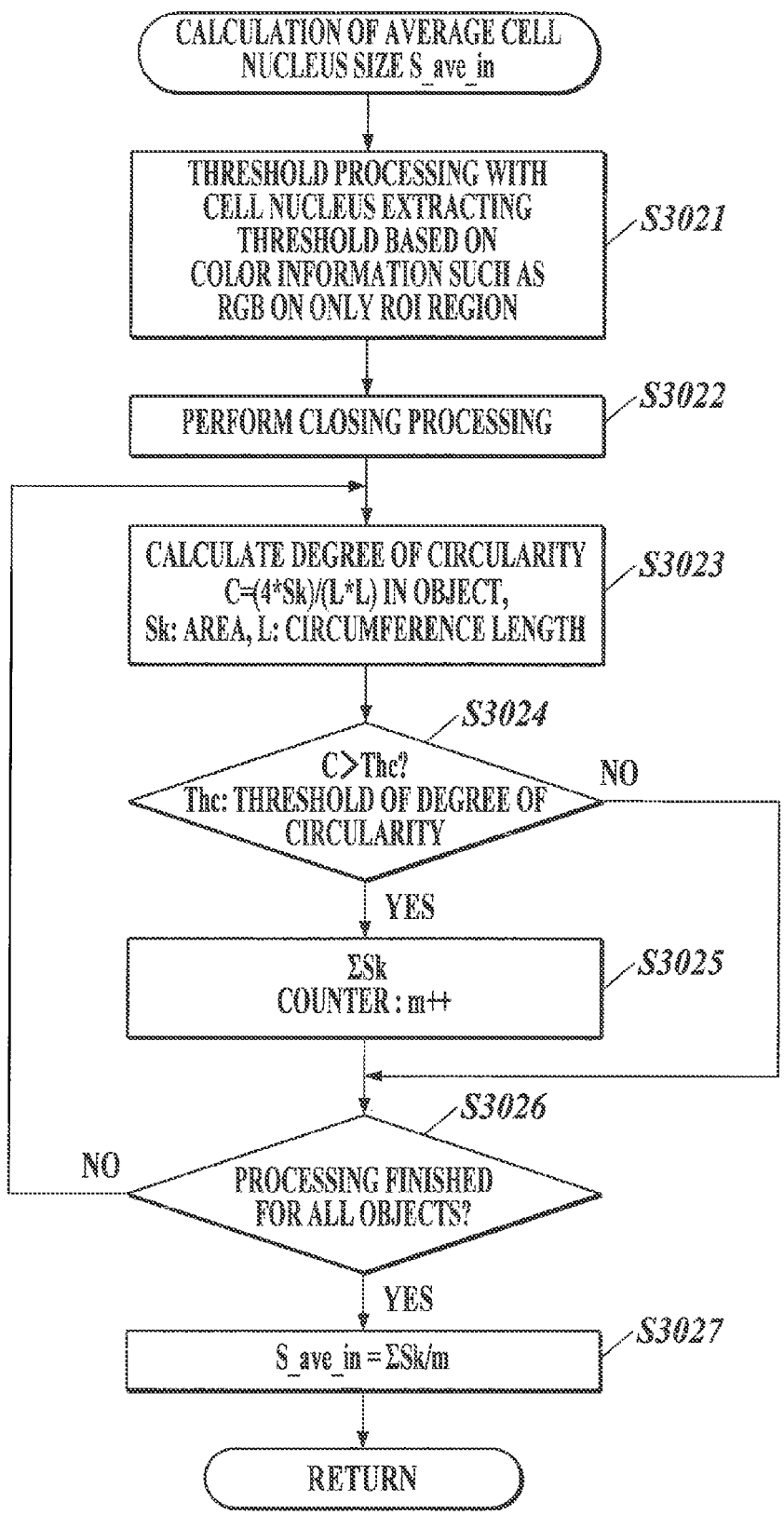
FIG. 16 is a flowchart showing a detailed flow of processing of step S302 of FIG. 14.

FIG. 16 shows a detailed flow of the processing in step S302. The processing in step S302 is performed by the control section 21 in coordination with a program stored in the storage section 25.

Figure 17A:
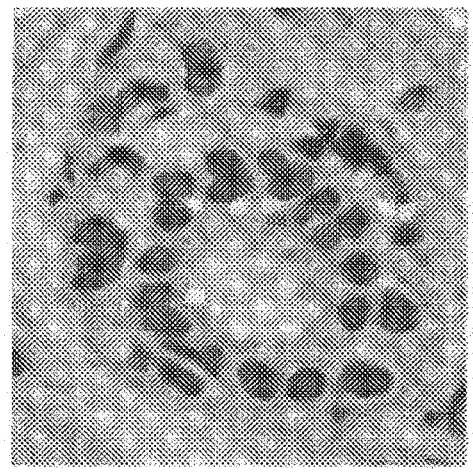
FIG. 17A is a diagrams showing a bright field image before threshold processing.
Figure 17B:
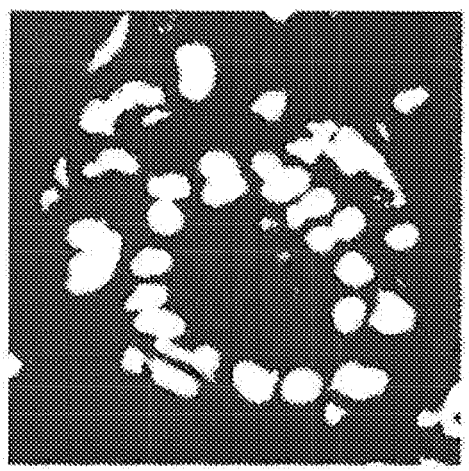
FIG. 17B is a diagram showing an image on which threshold processing is performed in the bright field image of FIG. 17A.

First, the threshold processing is performed on only the ROI region using the cell nucleus extracting threshold based on the color information such as RGB and the value of each pixel is binarized (step S3021). The cell nucleus extracting threshold is set in advance. FIG. 17A shows an original image, and FIG. 17B shows an image where the threshold processing is performed on the original image of FIG. 17A. In the bright field image where HE staining is performed, as shown in FIG. 17A, the cell nucleus is drawn with a density higher than the periphery. Therefore, as shown in FIG. 17B, the cell nucleus candidate can be extracted by performing the threshold processing.

Next, the closing processing is performed on the image after threshold processing, and a small region such as noise is removed (step S3022).

Next, the degree of circularity C of the object (cell nucleus candidate) extracted from the ROI region is calculated (step S3023). The degree of circularity C can be obtained by the following equation (1).

$$C = (4\pi \times Sk) \div (L \times L) \qquad \text{equation (1)}$$

Here, Sk is an area of the object, and L is a length of the periphery.

Figure 17C:
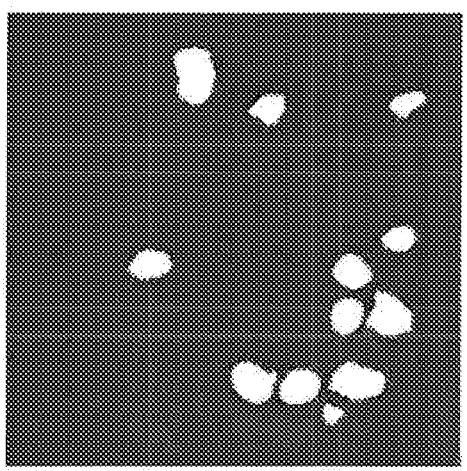
FIG. 17C is a diagram showing a result of extracting a cell nucleus with a degree of circularity of C>Thc from the cell nucleus candidate extracted in FIG. 17B.

Next, the calculated degree of circularity C is compared with a predetermined threshold Thc. When it is judged that it is not C>Thc (step S3024; NO), the processing advances to step S3026. When it is judged that it is C>Thc (step S3024; YES), the area of the object Sk is added ($\Sigma$Sk) and the counter m is incremented by 1 (step S3025). With this, the processing advances to step S3026. FIG. 17C shows a result of extracting a cell nucleus with a degree of circularity of C>Thc from the cell nucleus candidate extracted in FIG. 17B.

In step S3026, it is judged whether the calculation of the degree of circularity C is finished for all of the objects in the ROI region. When it is judged that there is an object in which the calculation of the degree of circularity C is not finished (step S3026; NO), the processing returns to step S3023, and the processing of step S3023 to step S3025 is performed for the next object. When it is judged that the calculation of the degree of circularity is finished for all of the objects in the ROI region (step S3026; YES), $\Sigma$Sk is divided by m, the average cell nucleus size S_ave_in is calculated (step S3027), and the processing advances to step S303 of FIG. 14.

In step S303 of FIG. 14, the basis cell nucleus size S_base stored in the storage section 25 is referred (step S303). Then, the average cell nucleus size S_ave_in is divided by the basis cell nucleus size S_base, and an estimated enlargement percentage Mag is calculated (step S304).

Figure 18:
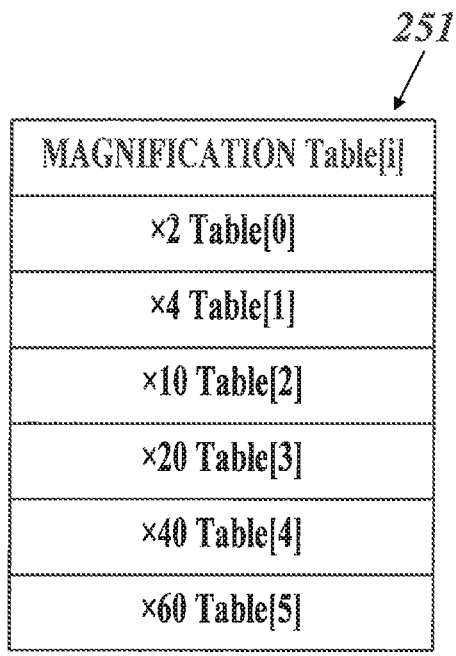
FIG. 18 is a diagram showing an example of a magnification table.

When the estimated enlargement percentage Mag is calculated, the capturing magnification of the bright field image is determined based on the magnification table 251 stored in the storage section 25 and the estimated enlargement percentage Mag (step S305). FIG. 18 shows an example of the magnification table 251. In step S305, based on the magnification table 251 and the estimated magnification percentage Mag, the capturing magnification used in capturing is determined among, for example, 6 capturing magnifications used in microscopic observation. The content of the magnification table 251 is not limited to what is shown in FIG. 18, and the content differs depending on the capturing magnification which can be used for capturing in the microscopic image obtaining apparatus 1A.

FIG. 19 shows a detailed flow of the processing in step S305. The processing of step S305 is performed by the control section 21 in coordination with a program stored in the storage section 25.

First, 5 is set in the variable i (step S3051).

Next, it is judged whether Mag≥Table [i] (step S3052). When it is judged that it is Mag≥Table [i] (step S3052; YES), the capturing magnification is determined to be Table [i] (step S3053), and the processing advances to step S306 of FIG. 14.

When it is judged that it is not Mag≥Table [i] (step S3052; NO), variable i is decremented (step S3054), and then it is judged whether i≥0 (step S3055). When it is judged that it is i≥0 (step S3055; YES), the processing returns to step S3052. When it is judged that it is not i≥0 (step S3055; NO), the capturing magnification is determined to be equal magnification (step S3056), and the processing advances to step S306 of FIG. 14.

In step S306, the cell region is estimated based on the determined capturing magnification and the region of the cell nucleus extracted in step S2 of FIG. 10 (step S306). The radius r which corresponds to each capturing magnification defined in the magnification table 251 is stored in the storage section 25 in advance. In step S306, the radius r corresponding to the determined capturing magnification is obtained, and the circular region of the radius r with the centroid of each cell nucleus as the center is determined. The centroid of the cell nucleus can be calculated by the following [Formula 1].

$$\text{centroid } (x,y) = \Sigma(\text{Label\_cell\_}x/\text{count}, \text{Label\_cell\_}y/\text{count}) \quad \text{[Formula 1]}$$

Figure 20A:
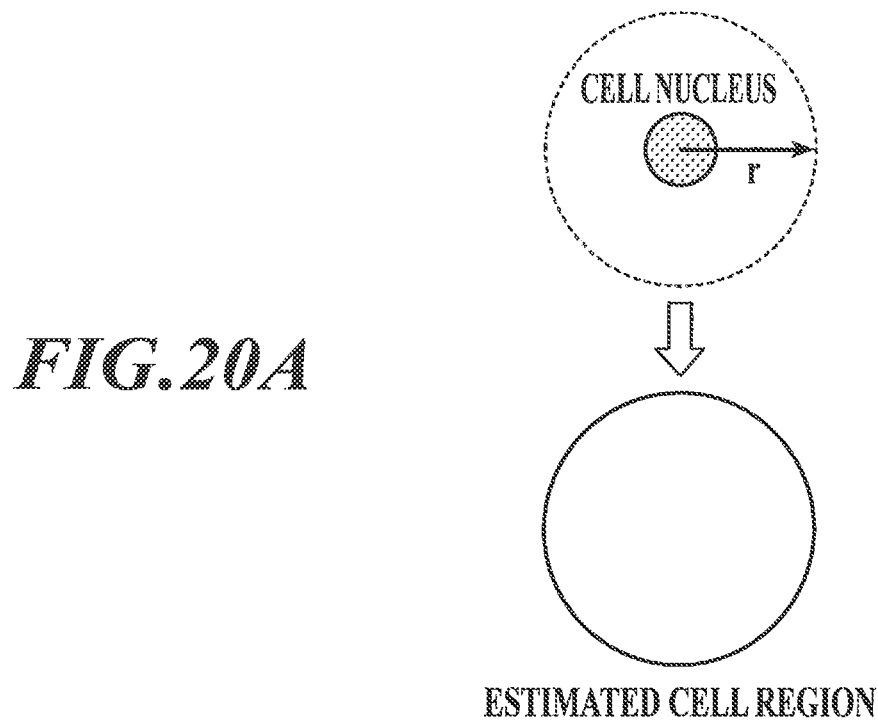
FIG. 20A is a diagram describing a cell region including one cell.
Figure 20B:
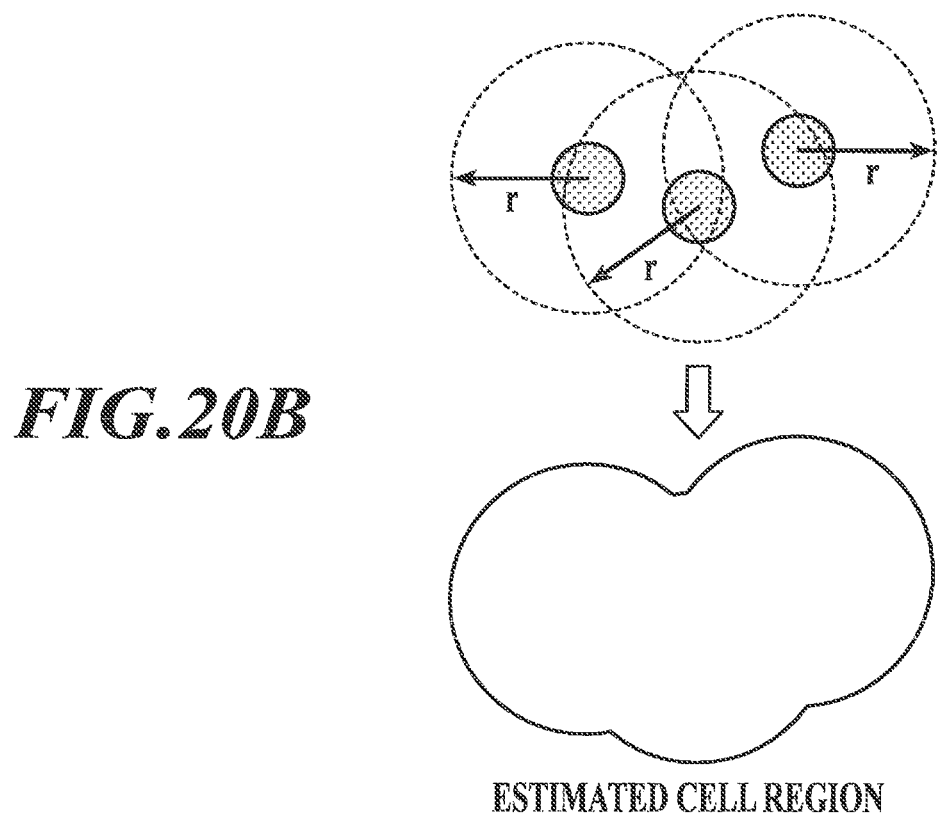
FIG. 20B is a diagram describing a cell region including a plurality of cells.

Label_cell_x: x coordinate of cell region
Label_cell_y: y coordinate of cell region
count: pixel number of cell region Then, as shown in FIG. 20A, when the set circular region is not overlapped with another circular region, the set circular region is estimated as the cell region including one cell. As shown in FIG. 20B, when the plurality of set circular regions overlap each other, the region surrounded by the outer circumference of the plurality of overlapping circular regions is estimated as the cell region including a plurality of cells.

When the cell region is determined, the processing advances to step S6 of FIG. 10.

When a fluorescent image is input from a microscopic image obtaining apparatus 1A through the communication I/F 24 (step S4), the fluorescent bright point is extracted from the fluorescent image (step S5).

FIG. 21 shows a detailed flow of processing of step S5. The processing of step S5 is performed by the control section 21 in coordination with a program stored in the storage section 25.

First, an R component is extracted from the fluorescent image (step S501).

Figure 22:
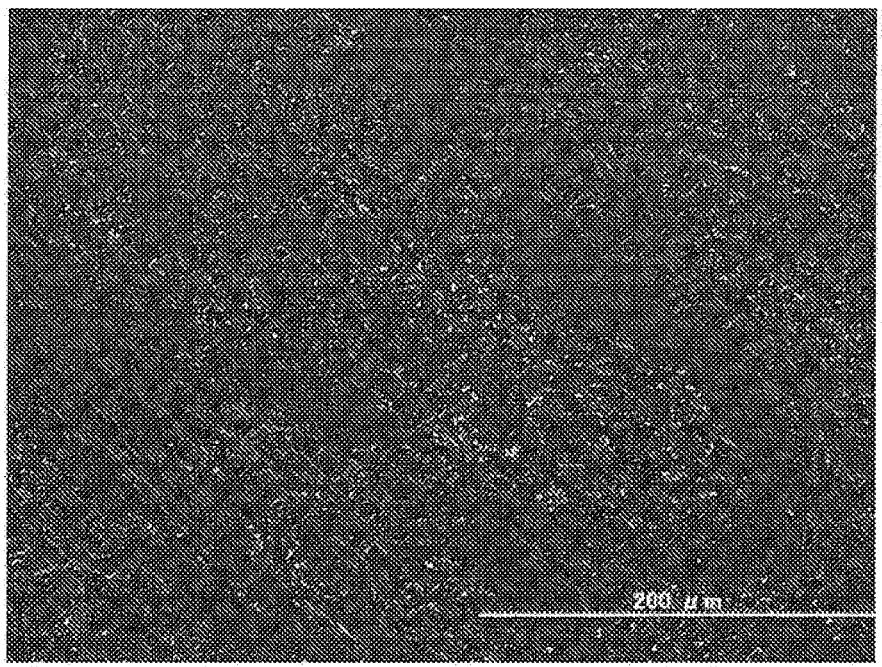
FIG. 22 is a diagram showing an example of a fluorescent bright point candidate image.

Next, Top hat conversion is performed on an image from which the R component is extracted (step S502). Top hat conversion is processing where a value of a pixel corresponding to the image of multiplying the minimum value filter and the maximum value filter to the input image in this order is subtracted from the value of each pixel of the input image. The minimum value filter replaces the value of the target pixel with the minimum value among the neighboring pixels (for example, 3×3 pixels) of the target pixel. The maximum value filter replaces the value of the target pixel with the maximum value among the neighboring pixels (for example, 3×3 pixels) of the target pixel. According to Top hat conversion, a small projection (region where brightness is high compared to neighboring pixels) on a gradation profile can be extracted. With this, the fluorescent bright point candidate image can be obtained. FIG. 22 shows an example of a fluorescent bright point candidate image.

Figure 23:
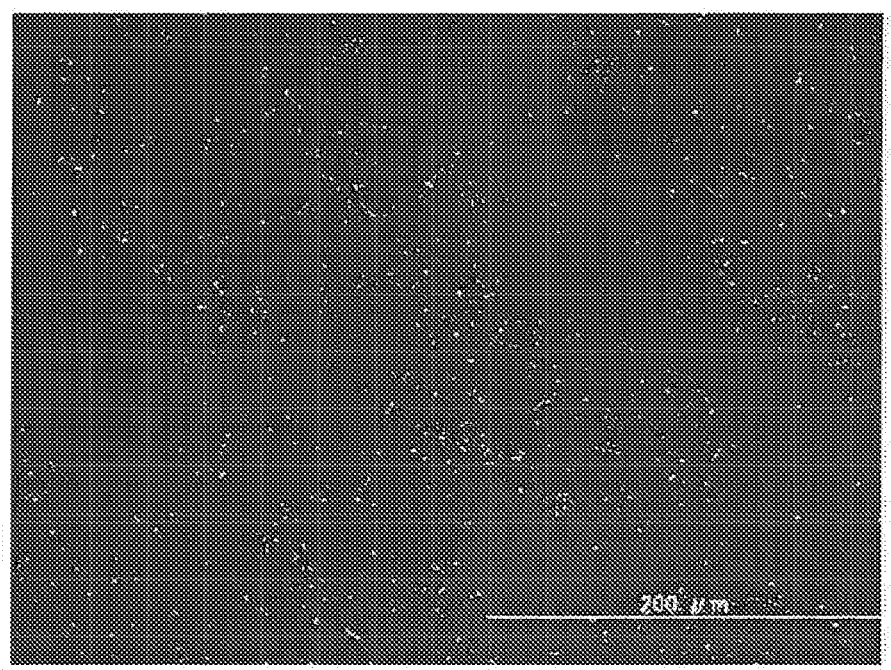
FIG. 23 is a diagram showing an example of a fluorescent bright point image obtained after noise removal in the fluorescent bright point candidate image shown in FIG. 16.

Next, noise is removed from the fluorescent bright point candidate image, and the image (fluorescent bright point image) with the fluorescent bright point extracted is obtained (step S503). FIG. 23 shows the image with the fluorescent bright point extracted obtained after noise removal from the fluorescent bright point candidate image shown in FIG. 22.

Then, after labeling processing is performed on the image after noise removal, the label Label_point is attached to each of the extracted fluorescent bright point (step S504). Label_point is attached in order from 1. After the labeling processing ends, the processing advances to step S6 of FIG. 10.

In step S6 of FIG. 10, the value of each pixel of the cell nucleus image and the value of the pixel corresponding to the fluorescent bright point image are added (step S6), and the feature amount regarding the fluorescent bright point and the cell nucleus in the cell region is calculated from the added image (step S7).

Here, since the cell proliferates in the region where the cancer is expressed, when the cell region is a cancer region, the number of cell nuclei n in the region becomes larger compared to normal cases. In other words, the area occupied by each cell nucleus in the region becomes smaller. In step S7, S/n which is the area occupied by each cell nucleus in the region and which is a feature amount showing the number of cell nuclei in the cell region is calculated as one of the feature amounts.

For example, when the area of the cell region is $\pi r^2$, in the cell region which includes only 1 cell nucleus, since the number of cell nuclei n is 1, and the area of the cell region is $\pi r^2$, the area S/n occupied by each cell nucleus is $\pi r^2$. In the cell region which includes 2 cell nuclei, since the number of cell nuclei n is 2, and the area of the cell region is $\pi r^2$, the area S/n occupied by each cell nucleus is $\pi r^2/2$. The smaller the area S/n is, the possibility of cancer becomes higher.

Since the cell proliferates in the region where the cancer is expressed, the cell nuclei is distributed unevenly, the number of cells increase, and the distance between the cells become closer. In step S7, an index value Fnum which is designed to show a larger value as the number of cell nuclei in the cell region becomes larger and the distance between the cell nuclei becomes closer is calculated as one of the feature amounts.

In calculating the Fnum, first, distance D(Ni) from cell nucleus Ni (i=1, . . . , n) to another cell nucleus N1 to Nn (excluding Ni) is calculated in each cell region. For example, D(Ni) of the cell nucleus Ni and cell nucleus Ni+1 can be calculated from the following [Formula 2].

$$D(N_i) = \sqrt{(x_{i+1}-x_i)^2+(y_{i+1}-y_i)^2} \quad \text{[Formula 2]}$$

Next, the minimum value Min(D(Ni)) of D(Ni) is calculated.

Figure 24:
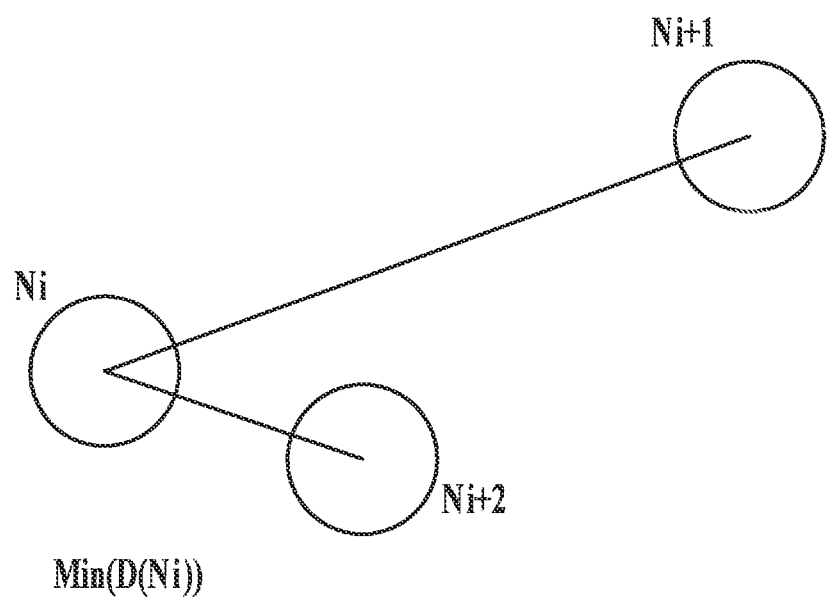
FIG. 24 is a diagram describing Min (D(Ni))

For example, as shown in FIG. 24, when there are 3 cell nuclei Ni, Ni+1, and Ni+2 (distance from Ni to Ni+1>distance from Ni to Ni+2) in the cell region, the distance from Ni to Ni+2 is calculated as Min(D(Ni)).

Then, Fnum is calculated for each cell region with [Formula 3] using the calculated Min (D(Ni)).

$$Fnum = n(n-1)\left(\sum_{i=1}^{n} \frac{1}{\text{Min}(D(Ni))}\right) \quad \text{[Formula 3]}$$

Moreover, since the specific protein is overexpressed in the cell membrane periphery of the cell in which cancer is expressed, the density of the fluorescent bright point in the region becomes high when the cell region is the cancer region. In step S7, density $D_k$ of the fluorescent bright point in each cell region is calculated as one of the feature amounts.

For example, when the number of fluorescent bright points in the cell region is H, the area is S, and the number of cell nuclei is n, the bright point density $D_k$ in the cell region can be obtained by the following equation (2).

$$D_k = (H/S)/n \quad \text{equation (2)}$$

$D_k$ is an index quantitatively showing the expression amount of the specific protein in the cell region.

As the $D_k$ becomes larger, the degree of malignancy of the cancer in the cell region becomes higher.

When the calculation of the feature amount ends, whether each cell region is a cancer region and the protein expression status in the cancer region are determined based on the calculated feature amount (step S8).

Figure 25:
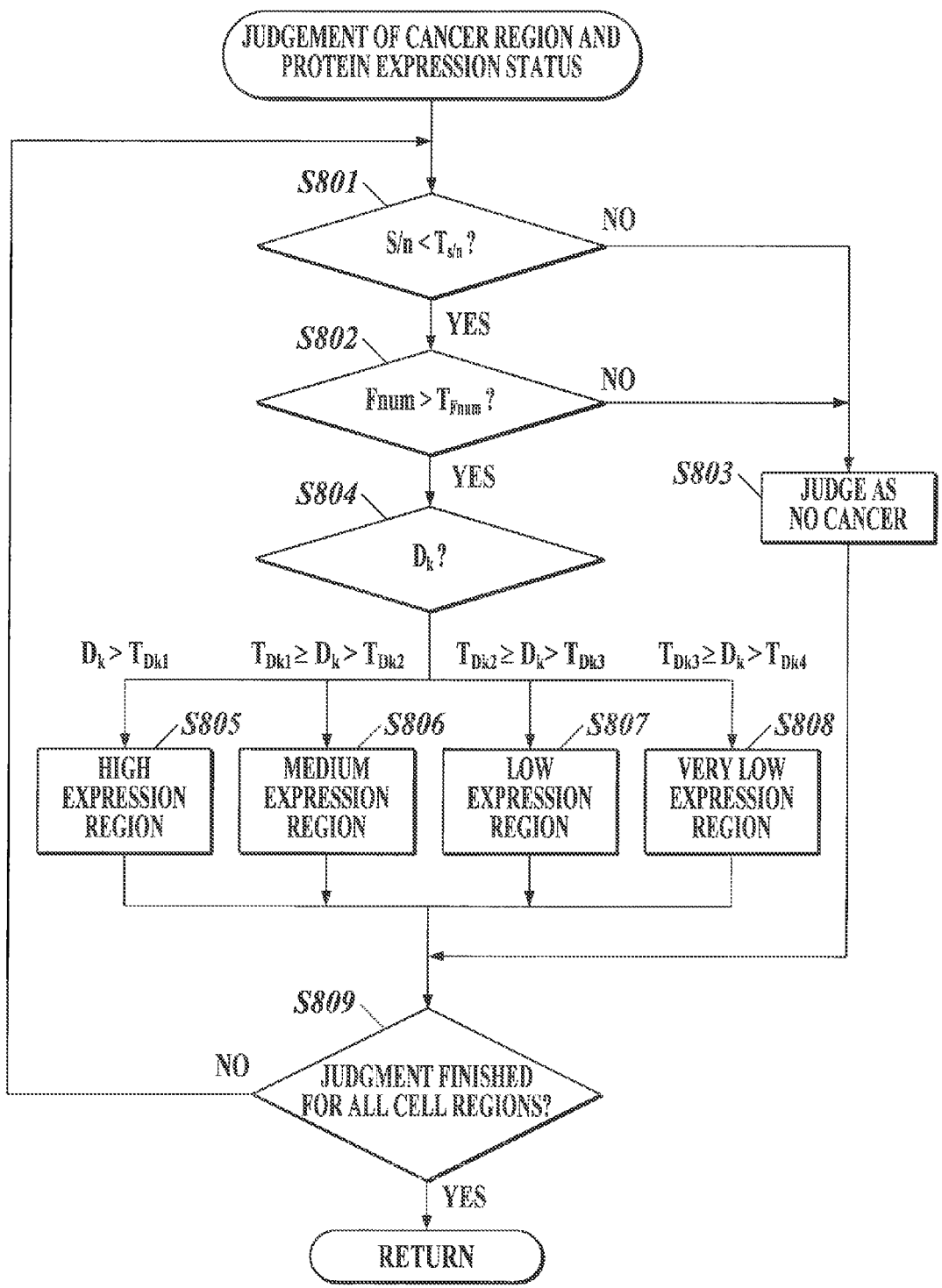
FIG. 25 is a flowchart showing details of processing of step S8 of FIG. 10.

FIG. 25 shows a detailed flow of the processing of step S8 of FIG. 10. The processing of step S8 is performed by the control section 21 in coordination with a program stored in the storage section 25.

First, the cell region of the determination target is selected, and it is judged whether S/n is smaller than the predetermined threshold $T_{S/n}$ (step S801). When it is judged that S/n is not smaller than the predetermined threshold $T_{S/n}$ (step S801; NO), it is determined that the region is not a cancer region (no cancer) (step S803), and the processing advances to step S809.

When it is judged that S/n is smaller than a predetermined threshold $T_{S/n}$ (step S801; YES), it is judged whether Fnum exceeds a predetermined threshold $T_{Fnum}$ (step S802). When it is judged that Fnum does not exceed a predetermined threshold $T_{Fnum}$ (step S802; NO), it is determined that the region is not a cancer region (no cancer) (step S803), and the processing advances to step S809.

When it is judged that Fnum exceeds a predetermined threshold $T_{Fnum}$ (step S803; YES), the region is determined to be cancer, and $D_k$ is compared with predetermined thresholds $T_{Dk1}$, $T_{Dk2}$, $T_{Dk3}$, and $T_{Dk4}$ (step S804). Here, $T_{Dk1} > T_{Dk2} > T_{Dk3} > T_{Dk4}$.

When it is judged that $D_k > T_{Dk1}$ (step S804; $D_k > T_{Dk1}$), the cell region is determined to be a high expression region of the specific protein (step S805), and the processing advances to step S809.

When it is judged that $T_{Dk1} \geq D_k > T_{Dk2}$ (step S804; $T_{Dk1} \geq D_k > T_{Dk2}$), the cell region is determined to be a medium expression region of the specific protein (step S806), and the processing advances to step S809.

When it is judged that $T_{Dk2} \geq D_k > T_{Dk3}$ (step S804; $T_{Dk2} \geq D_k > T_{Dk3}$), the cell region is determined to be a low expression region of the specific protein (step S807), and the processing advances to step S809.

When it is judged that $T_{Dk3} \geq D_k > T_{Dk4}$ (step S804; $T_{Dk3} \geq D_k > T_{Dk4}$), the cell region is determined to be a very low expression region of the specific protein (step S808), and the processing advances to step S809.

In step S809, it is judged whether determination of all of the cell regions is finished. When it is judged that the determination of all of the cell regions is not finished (step S809; NO), the processing returns to step S801, and the determination regarding the next cell region is performed. When it is judged that the determination of all of the cell regions is finished (step S809; YES), the processing advances to step S9 in FIG. 10.

In step S9 of FIG. 10, an analysis result screen 231 is generated including an image with the high expression region, the medium expression region, the low expression region, and the very low expression region displayed divided by a different display form (for example, discrimination by color) according to the classification on the bright field image, and the above is displayed on the display section 23 (step S9).

Figure 26:
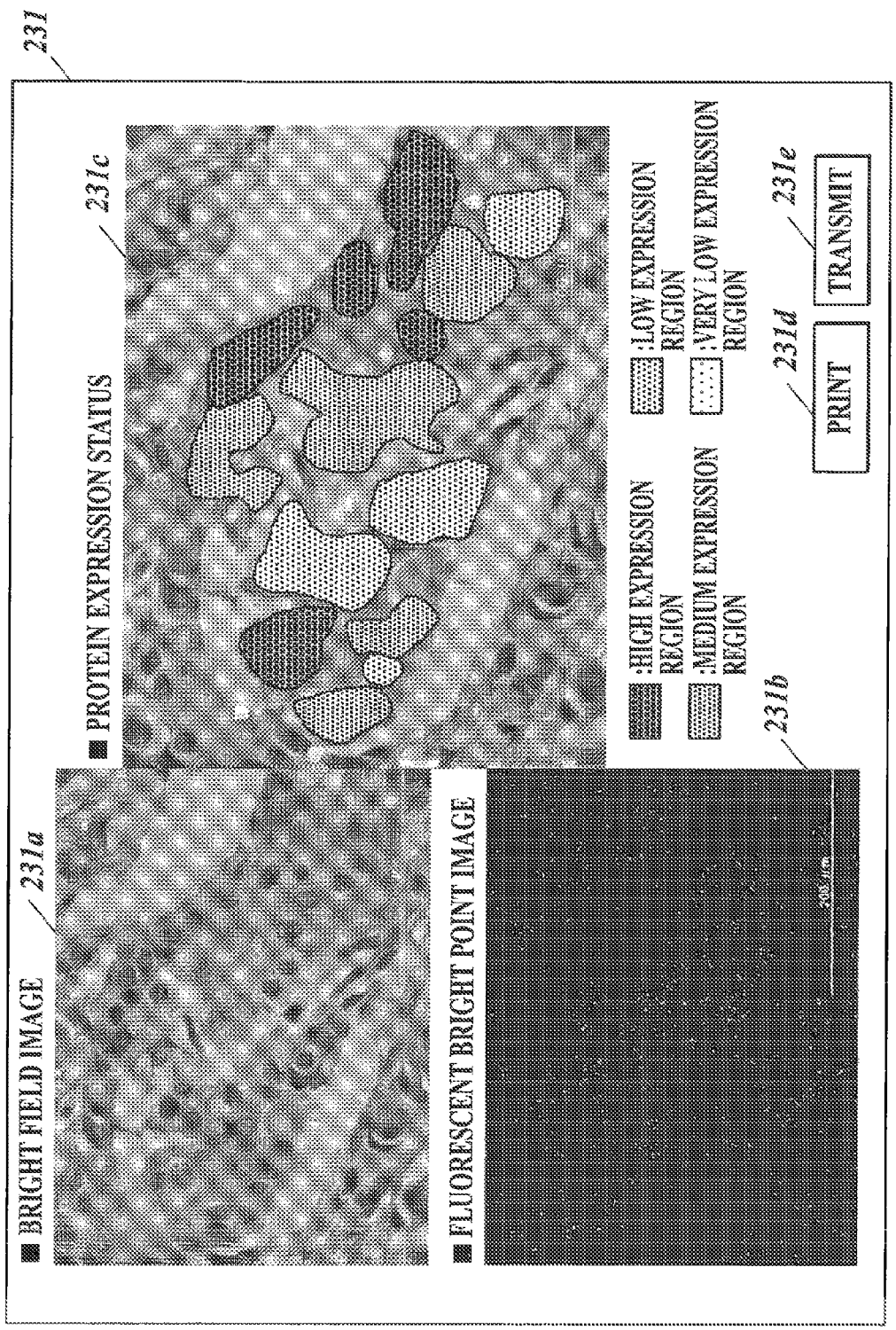
FIG. 26 is a diagram showing an example of an analysis result screen.

FIG. 26 shows an example of an analysis result screen 231. As shown in FIG. 26, the following are displayed in the analysis result screen 231, a bright field image 231a, a fluorescent bright point image 231b, and a protein expression status display 231c.

In the protein expression status display 231c, the high expression region, the medium expression region, the low expression region, and the very low expression region of the specific protein are displayed according to color on the bright field image. The regions displayed by the above color are regions determined to be cancer. Therefore, the physician is able to understand at a glance where the cancer is in the entire image of the tissue slice by looking at the analysis result screen 231. Therefore, it is possible to be cautious so as not to overlook the cancer in the large field. The region determined to be cancer is displayed in different color according to the status of expression of the specific protein. Therefore, the physician is able to efficiently understand overexpression of the specific protein and how it spreads which are the index showing degree of malignant of cancer. With this, the physician is able to conceive a suitable treatment plan.

The display method of the analysis result screen 231 is not limited to those shown in FIG. 26. For example, only the protein expression status display 231c can be displayed. Moreover, the display can be switched between the bright field image and the protein expression status display according to an instruction to switch on the operation section 22. Moreover, either one or all of the bright field image 231a, the fluorescent bright point image 231b, and the protein expression status display 231c displayed in the analysis result screen 231 can be displayed enlarged or reduced for ease of observation.

The analysis result can be printed by pressing the print button 231d or output to external devices by pressing the transmit button 231e.

When the print button 231d is pressed on the operation section 22, the control section 21 transmits the data of the analysis result to a printer which is not shown through the communication I/F 24 or a communication network such as a LAN, etc., and the analysis result is printed. Alternatively, when the transmit button 231e is pressed on the operation section 22, the control section 21 transmits the data of the analysis result to the external device (for example, PACS (Picture Archiving and Communication System for medical application)) through the communication I/F 24 or the communication network such as a LAN, etc.

As described above, according to the image processor 2A, the control section 21 extracts the region of the cell nucleus from the bright field image capturing the slide of the tissue slice. The control section 21 sets a circular region with a predetermined radius which includes from the centroid of the region of each extracted cell nucleus to the specific protein expression region of the cell membrane periphery. When the set circular region does not overlap with other circular regions, the set circular region is estimated to be a cell region including one cell. When a plurality of the set circular regions overlap on each other, the region surrounded by the outer circumference of the plurality of the overlapping circular regions is estimated to be the cell region including the plurality of cells. Moreover, the control section 21 extracts the fluorescent bright point from the fluorescent image captured with the same field. Then, based on the cell nucleus and the fluorescent bright point in each estimated cell region, the feature amount of each cell region is calculated. Whether each estimated cell region is cancer and the expression status of the specified cancer in the region determined to be cancer is determined based on the calculated feature amount, and the determination result is output.

Therefore, the physician is able to efficiently understand the cancer region and the expression status of the specific protein in the cancer region without overlooking the cancer from the entire image of the tissue slice.

For example, the control section 21 determines whether each cell region is cancer based on the area each cell nucleus occupies in each cell region and/or the index value showing the uneven distribution of the cell nucleus in the cell region. Then, the control section 21 determines the expression status of the specific protein in the region based on the density of the fluorescent bright point in the cell region determined to be cancer. Therefore, it is possible to accurately extract the cancer region using the feature of the cell of the cancer region such as the cell proliferating and the distance between the cell nuclei becoming shorter in the cancerous region. Moreover, the expression status of the specific protein in the region determined to be the cancer region can be accurately obtained by using the density of the fluorescent bright point.

Moreover, the control section 21 classifies the expression status of the specific protein in the cell region determined to be cancer into a plurality of levels based on whether the calculated feature amount of the fluorescent bright point in the cell region determined to be cancer exceeds a plurality of predetermined thresholds. The control section outputs an image dividing the cell region determined to be cancer on the cell shape image in a form according to the classified result of the expression status of the specific protein as the determination result. Therefore, the physician is able to understand at a glance where the cancer is in the entire image of the tissue slice in the region estimated to be the cell region. Therefore, the physician is able to be cautious to prevent overlooking the cancer in the large field. Moreover, the region determined to be cancer is displayed in a form different according to the expression status of the specific protein. Therefore, the physician is able to efficiently understand the overexpression of the specific protein and its spreading which is to be the index of the degree of malignity of the cancer. With this, the physician is able to conceive a suitable treatment plan.

The description of the above described embodiment is a suitable example of the present invention, and the present invention is not limited to the above.

For example, as one preferable example, according to the above embodiment, it is determined whether each cell region is cancer using the area occupied by each nucleus and the index value showing the uneven distribution of the cell nucleus in each cell region, and the expression status of the protein is determined using the number of fluorescent bright points in the region determined to be the cancer region. However, the method of determining whether the region is the cancer region and determining the expression status of the protein is not limited to the above. For example, either the area occupied by each nucleus or the index value showing the uneven distribution of the cell nucleus in each cell region can be used to determine whether the region is the cancer region. The number of fluorescent bright points can be used to determine whether the region is the cancer region.

For example, according to the above embodiment, HER2 protein in breast cancer is described as the example of the specific protein, however, the protein is not limited to the above. By changing the biological substance recognition site when the fluorescent image is obtained according to the type of lesion (cancer) which is to be the target of diagnosis, it is possible to provide the physician with the feature amount quantitatively showing the expression amount of the specific protein according to the type of lesion.

The above description discloses an example which uses an HDD, a semiconductor nonvolatile memory, or the like as the computer readable medium of the program of the present invention, however, the present invention is not limited to the above. A portable recording medium such as a CD-ROM, etc. can be applied as other computer readable media. A carrier wave can be applied as the medium which provides the data of the program of the present invention through a communication line.

The detailed configuration and the detailed operation of each device composing the pathological diagnosis assistance system 100 can be suitably changed within the scope of the present invention.

The entire disclosure of Japanese Patent Application No. 2012-078722 filed on Mar. 30, 2012 including description, claims, drawings, and abstract are incorporated herein by reference in its entirety.

Industrial Applicability

The present invention can be used in the field of medicine as a medical image processor which processes a microscopic image of a tissue slice.

Description of Reference Numerals

100 pathological diagnosis assistance system
1A microscopic image obtaining apparatus
2A image processor
21 control section
22 operation section
23 display section
24 communication I/F
25 storage section
26 bus
3A cable

The invention claimed is:

1. A medical image processor comprising:
   an input unit to input a cell shape image showing a shape of a cell in a tissue slice and a fluorescent image showing expression of a specific protein in a same range of the tissue slice as a fluorescent bright point;
   a cell nucleus extracting unit which extracts a region of a cell nucleus from the cell shape image;
   a fluorescent bright point extracting unit which extracts a fluorescent bright point from the fluorescent image;
   a region estimating unit which sets a predetermined region which includes from a centroid of a region of each cell nucleus extracted by the cell nucleus extracting unit to an expression region of the specific protein in a cell membrane periphery, wherein when the set region does not overlap with another set region, the set region is estimated to be a cell region including one cell, and when a plurality of the set regions overlap with each other, a region surrounded by an outer circumference of the plurality of overlapping regions is estimated to be a cell region including a plurality of cells;
   a feature amount calculating unit which calculates a feature amount regarding each cell region based on a cell nucleus and a fluorescent bright point included in each cell region estimated by the region estimating unit;
   a determining unit which determines whether each cell region estimated by the region estimating unit is cancer and which determines an expression status of the specific protein in the region determined to be cancer, the determinations being based on the calculated feature amount; and
   an output unit which outputs a determination result by the determining unit.

2. The medical image processor of claim 1, wherein, the region set by the region estimating unit is a circular region with a centroid of the region of each cell nucleus extracted by the cell nucleus extracting unit as a center and a predetermined radius including the expression region of the specific protein in the cell membrane periphery.

3. The medical image processor of claim 1, wherein,
the feature amount calculating unit calculates an area which each cell nucleus occupies in each cell region and/or an index value which shows uneven distribution of the cell nucleus in each cell region based on the cell nucleus included in each cell region estimated by the region estimating unit and calculates a density of the fluorescent bright point in each cell region based on the fluorescent bright point included in each cell region; and
the determining unit determines whether each cell region is cancer based on the area which each cell nucleus occupies in each cell region and/or the index value which shows uneven distribution of the cell nucleus in each cell region, and determines the expression status of the specific protein in the cell region determined to be cancer based on the density of the fluorescent bright point in the cell region.

4. The medical image processor of claim 1, wherein,
the determining unit classifies the expression status of the specific protein in the cell region determined to be cancer into a plurality of levels based on whether the calculated feature amount of the fluorescent bright point in the cell region determined to be cancer exceeds a plurality of predetermined thresholds; and
the output unit outputs an image dividing the cell region determined to be cancer on the cell shape image in a form according to a classification result of the expression status of the specific protein as the determination result.

5. A non-transitory computer-readable storage medium including a program for controlling a computer to function as:
an input unit to input a cell shape image showing a shape of a cell in a tissue slice and a fluorescent image showing expression of a specific protein in a same range of the tissue slice as a fluorescent bright point;
a cell nucleus extracting unit which extracts a region of a cell nucleus from the cell shape image;
a fluorescent bright point extracting unit which extracts a fluorescent bright point from the fluorescent image;
a region estimating unit which sets a predetermined region which includes from a centroid of a region of each cell nucleus extracted by the cell nucleus extracting unit to an expression region of the specific protein in a cell membrane periphery, wherein when the set region does not overlap with another set region, the set region is estimated to be a cell region including one cell, and when a plurality of the set regions overlap with each other, a region surrounded by an outer circumference of the plurality of overlapping regions is estimated to be a cell region including a plurality of cells;
a feature amount calculating unit which calculates a feature amount regarding each cell region based on a cell nucleus and a fluorescent bright point included in each cell region estimated by the region estimating unit;
a determining unit which determines whether each cell region estimated by the region estimating unit is cancer and which determines an expression status of the specific protein in the region determined to be cancer, the determinations being based on the calculated feature amount; and
an output unit which outputs a determination result by the determining unit.

* * * * *